(12) United States Patent
Robles, Jr. et al.

(10) Patent No.: US 9,572,725 B2
(45) Date of Patent: *Feb. 21, 2017

(54) ABSORBENT ARTICLES WITH MULTIPLE INDICATING WIDTHS

(71) Applicant: The Procter & Gamble Company, Cincinnati, OH (US)

(72) Inventors: Miguel Alvaro Robles, Jr., Wyoming, OH (US); Mattias Schmidt, Idstein (DE); Donald Carroll Roe, West Chester, OH (US); Kara Marie Cain, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 3 days.

This patent is subject to a terminal disclaimer.

(21) Appl. No.: 14/504,641

(22) Filed: Oct. 2, 2014

(65) Prior Publication Data
US 2015/0051565 A1    Feb. 19, 2015

Related U.S. Application Data

(63) Continuation of application No. 14/026,177, filed on Sep. 13, 2013, now Pat. No. 8,877,998, which is a
(Continued)

(51) Int. Cl.
*A61F 13/42*    (2006.01)
(52) U.S. Cl.
CPC .................................... *A61F 13/42* (2013.01)

(58) Field of Classification Search
CPC ........................... A61F 13/42; A61F 2013/422
(Continued)

(56) References Cited

U.S. PATENT DOCUMENTS

| | | | |
|---|---|---|---|
| 4,022,211 A | | 5/1977 | Timmons et al. |
| 4,231,370 A | * | 11/1980 | Mroz ...................... A61F 13/42 |
| | | | 116/206 |

(Continued)

FOREIGN PATENT DOCUMENTS

| | | |
|---|---|---|
| DE | 85 06 388 U1 | 6/1985 |
| DE | 20 2006 008161 | 3/2007 |

(Continued)

OTHER PUBLICATIONS

PCT International Search Report & Written Opinion, PCT/US2009/069559, mailed Feb. 17, 2010, 12 pages.
(Continued)

*Primary Examiner* — Susan Su
(74) *Attorney, Agent, or Firm* — Kathleen Y. Carter

(57) ABSTRACT

An absorbent article comprises a first location of a first portion of a visual fullness indicating area that is configured to change to a subsequent visual state when indicating the presence of a bodily exudate. At the first location, the first portion has a first overall width. The absorbent article also comprises a second location of a second portion of a visual fullness indicating area that is configured to change to a subsequent visual state when indicating the presence of a bodily exudate. The second location is outboard from the first location. The second location has a second overall width that is wider than the first overall width.

14 Claims, 11 Drawing Sheets

Related U.S. Application Data continuation of application No. 12/646,315, filed on Dec. 23, 2009, now Pat. No. 8,552,250, which is a continuation-in-part of application No. 12/346,481, filed on Dec. 30, 2008, now abandoned.

(58) Field of Classification Search
USPC .......................................................... 604/361
See application file for complete search history.

(56) References Cited

U.S. PATENT DOCUMENTS

| | | | |
|---|---|---|---|
| 4,507,121 A | 3/1985 | Leung | |
| 5,078,708 A | 1/1992 | Haque | |
| 5,354,289 A | 10/1994 | Mitchell et al. | |
| 5,435,010 A | 7/1995 | May | |
| 5,902,296 A * | 5/1999 | Fluyeras | A61F 13/42 604/361 |
| 6,297,424 B1 | 10/2001 | Olson et al. | |
| 6,307,119 B1 | 10/2001 | Cammarota et al. | |
| 6,710,221 B1 | 3/2004 | Pierce et al. | |
| 8,080,704 B2 * | 12/2011 | Uchida | A61L 15/56 604/361 |
| 8,383,876 B2 | 2/2013 | Robles et al. | |
| 2001/0008683 A1 | 7/2001 | Takai et al. | |
| 2002/0007162 A1 | 1/2002 | Cammarota et al. | |
| 2002/0016579 A1 | 2/2002 | Stenberg | |
| 2003/0078553 A1 | 4/2003 | Wada et al. | |
| 2003/0130631 A1 | 7/2003 | Springer et al. | |
| 2004/0078014 A1 * | 4/2004 | Shapira | A61F 13/42 604/361 |
| 2004/0138633 A1 * | 7/2004 | Mishima | A61F 13/42 604/361 |
| 2004/0254549 A1 | 12/2004 | Olson et al. | |
| 2004/0254550 A1 * | 12/2004 | Huang | A61F 13/42 604/361 |
| 2005/0065489 A1 | 3/2005 | Driskell et al. | |
| 2005/0124947 A1 | 6/2005 | Fernfors | |
| 2006/0025733 A1 * | 2/2006 | Kikuchi | A61F 13/42 604/361 |
| 2006/0069362 A1 | 3/2006 | Odorzynski et al. | |
| 2006/0149197 A1 | 7/2006 | Niemeyer et al. | |
| 2006/0149204 A1 | 7/2006 | Niemeyer et al. | |
| 2006/0229577 A1 | 10/2006 | Roe et al. | |
| 2006/0229578 A1 * | 10/2006 | Roe | A61F 13/42 604/361 |
| 2007/0197986 A1 | 8/2007 | Matsui | |
| 2007/0276348 A1 | 11/2007 | Stenberg | |
| 2008/0054408 A1 * | 3/2008 | Tippey | A61F 13/42 257/621 |
| 2008/0086060 A1 | 4/2008 | Kritzman et al. | |
| 2008/0147031 A1 | 6/2008 | Long et al. | |
| 2008/0208151 A1 | 8/2008 | Zacharias et al. | |
| 2008/0228157 A1 | 9/2008 | McKiernan et al. | |
| 2010/0069862 A1 * | 3/2010 | Wada | A61F 5/451 604/361 |
| 2010/0168695 A1 | 7/2010 | Robles et al. | |
| 2010/0168696 A1 | 7/2010 | Robles et al. | |
| 2010/0168697 A1 | 7/2010 | Robles et al. | |
| 2010/0168698 A1 | 7/2010 | Robles et al. | |
| 2010/0168699 A1 | 7/2010 | Robles et al. | |
| 2010/0168700 A1 | 7/2010 | Schmidt et al. | |
| 2010/0168701 A1 | 7/2010 | Schmidt et al. | |
| 2011/0112497 A1 | 5/2011 | Shiraishi et al. | |
| 2013/0123727 A1 | 5/2013 | Ichihara et al. | |
| 2013/0307570 A1 | 11/2013 | Bosaeus et al. | |

FOREIGN PATENT DOCUMENTS

| | | |
|---|---|---|
| EP | 0 705 089 B1 | 5/1997 |
| EP | 0 925 769 A2 | 6/1999 |
| EP | 1 216 673 B1 | 10/2005 |
| FR | 2 695 824 B1 | 3/1994 |
| JP | 2001-095845 | 4/2001 |
| JP | 2005-127933 A2 | 5/2005 |
| KR | 98039173 | 8/1998 |
| KR | 100484478 B1 | 4/2005 |
| WO | WO 95/00099 A1 | 1/1995 |
| WO | WO 99/16401 | 4/1999 |
| WO | WO 99/56690 A1 | 11/1999 |
| WO | WO 01/95845 A1 | 12/2001 |
| WO | WO 2005/030084 A2 | 4/2005 |
| WO | WO 2005/039656 A1 | 5/2005 |
| WO | WO 2005/102238 A1 | 11/2005 |
| WO | WO 2006/110428 A1 | 10/2006 |
| WO | WO 2008/072116 A1 | 6/2008 |

OTHER PUBLICATIONS

All Office Actions, U.S. Appl. No. 12/646,296.
All Office Actions, U.S. Appl. No. 12/646,334.
All Office Actions, U.S. Appl. No. 12/646,354.
All Office Actions, U.S. Appl. No. 12/646,393.
All Office Actions, U.S. Appl. No. 12/646,414.
All Office Actions, U.S. Appl. No. 12/646,430.
International Search Report, PCT/US2009/069569, mailed May 19, 2010, 17 pages.
International Search Report, PCT/US2009/069579, mailed Apr. 22, 2010, 12 pages.
International Search Report, PCT/US2009/069570, mailed Apr. 22, 2010, 12 pages.
International Search Report, PCT/US2009/069572, mailed May 7, 2010, 16 pages.
International Search Report, PCT/US2009/069659, mailed Jun. 7, 2010, 17 pages.
International Search Report, PCT/US2009/069656, mailed Jun. 7, 2010, 17 pages.

* cited by examiner

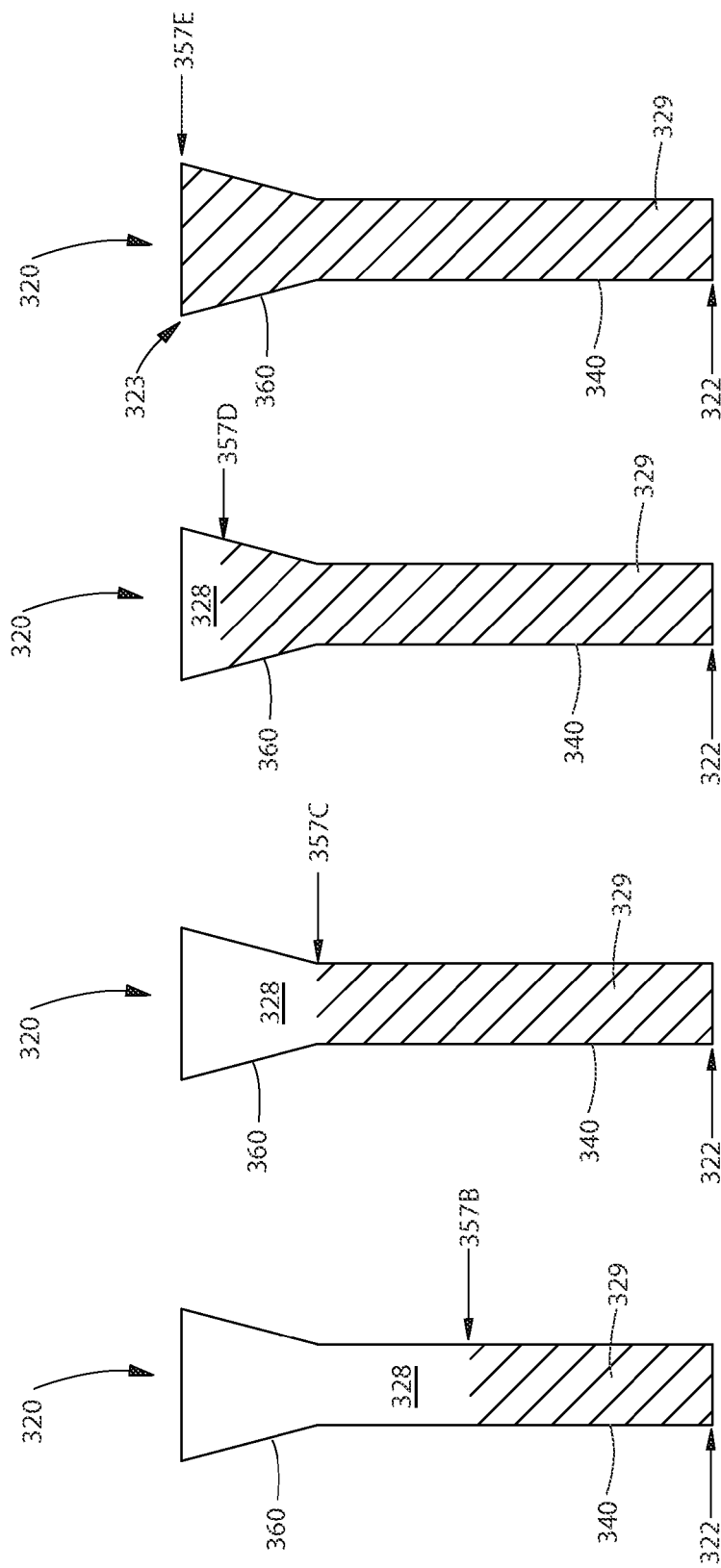

ABSORBENT ARTICLES WITH MULTIPLE INDICATING WIDTHS

FIELD

In general, embodiments of the present disclosure relate to wetness indicating for absorbent articles. In particular, embodiments of the present disclosure relate to visual fullness indicating for absorbent articles.

BACKGROUND

Absorbent articles can absorb liquid bodily exudates such as sweat, blood, urine, menses, etc. An absorbent article can include a wetness indicator. The wetness indicator can indicate the presence of a liquid bodily exudate in the article. Unfortunately, some wetness indicators for absorbent articles can be difficult to understand. If the signal from a wetness indicator is misunderstood then the absorbent article may be changed too soon. The wearer may underutilize the capacity of the article. If the signal from a wetness indicator is misunderstood then the absorbent article may be changed too late. The bodily exudates may exceed the capacity of the article resulting in leaks.

BRIEF DESCRIPTION OF THE DRAWINGS

FIG. 3B illustrates a subsequent state of indication for the visual fullness indicator of FIG. 3A, according to embodiments of the present disclosure.

FIG. 3C illustrates a subsequent state of indication for the visual fullness indicator of FIG. 3B, according to embodiments of the present disclosure.

FIG. 3D illustrates a subsequent state of indication for the visual fullness indicator of FIG. 3C, according to embodiments of the present disclosure.

FIG. 3E illustrates a subsequent state of indication for the visual fullness indicator of FIG. 3D, according to embodiments of the present disclosure.

SUMMARY

Figure 1A:
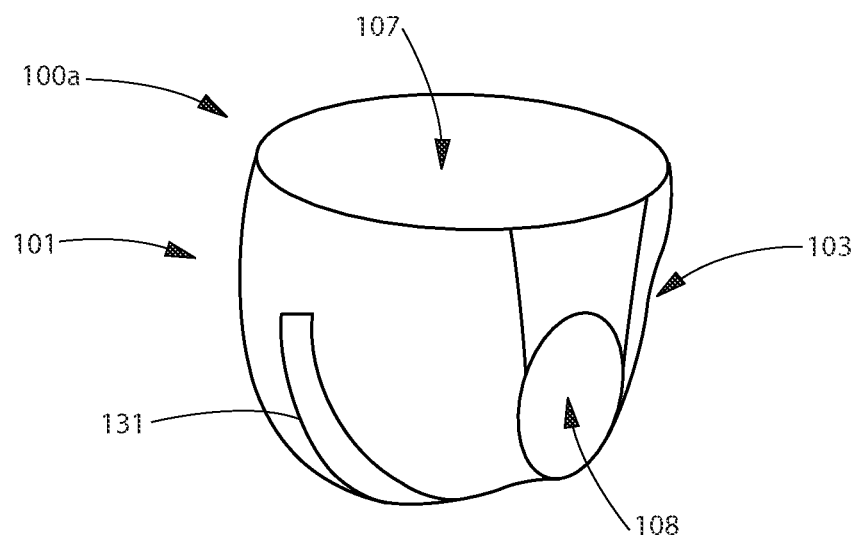
FIG. 1A illustrates a pant-type disposable wearable absorbent article with a visual fullness indicator in the front, according to embodiments of the present disclosure.

The present disclosure includes absorbent articles with wetness indicators that are easy to understand. The wetness indicators are easy to understand because they have multiple widths.

As an example, an absorbent article can have an inboard visual fullness indicating area with a narrower width and an outboard visual fullness indicating area with a wider width. The visual fullness indicating areas can change visual states in sequence; first the narrower inboard visual fullness indicating area, then the wider outboard visual fullness indicating area.

The width of the changed portion can indicate how full the absorbent article is. For instance, a change in visual state in the narrower inboard portion can indicate that the absorbent article is somewhat filled while a change in visual state in the wider outboard portion can indicate that the absorbent article is approaching full. Throughout the present disclosure, unless otherwise indicated, the terms narrower and wider are used relative to each other; that is a wider width is wider than a narrower width and a narrower width is narrower than a wider width. The visual state changes in these different widths can provide differing visual signals. These differing visual signals can be easily understood as indicating differing degrees of fullness.

An absorbent article having multiple indicating colors can help provide certainty about the fullness of the absorbent article. By knowing how full an article is, the article can be changed after the wearer has appropriately utilized the capacity of the article. Also, by knowing how full an article is, the article can be changed before it is likely to leak.

DETAILED DESCRIPTION

The multiple indicating widths of the present disclosure can be used with all kinds of absorbent articles. An absorbent article can absorb liquid bodily exudates such as sweat, blood, urine, menses, etc. An absorbent article can be a product or a material. Examples of absorbent articles include products and/or materials for sanitary protection, hygienic use, and/or wound care.

Some absorbent articles are disposable. A disposable absorbent article is configured to be partly or wholly disposed of after a single use. A disposable absorbent article is configured such that the soiled article, or a soiled portion of the article, is not intended to be restored and reused (e.g., not intended to be laundered). Examples of disposable absorbent articles include wound care products, such as bandages and dressings, as well as feminine care products, such as pads and liners. Disposable absorbent articles can use embodiments of the present disclosure.

Some absorbent articles are wearable. A wearable absorbent article is configured to be worn on or around a body of a wearer. Wearable absorbent articles can also be disposable. Examples of disposable wearable absorbent articles include disposable diapers and disposable incontinence undergarments. A disposable wearable absorbent article can receive and contain bodily exudates while being worn by a wearer. In some embodiments, a disposable wearable absorbent article can include a topsheet, an absorbent core, an outer cover, a waist opening, and leg openings. Disposable wearable absorbent articles can use embodiments of the present disclosure.

One kind of wetness indicator for an absorbent article is a visual fullness indicator. A wetness indicator is considered visual if it can indicate the presence of a liquid bodily exudate by its visual state. Throughout the present disclosure, unless otherwise stated, the presence of a liquid bodily exudate refers to the presence of a concentration of the liquid bodily exudate that is sufficient to cause a visual wetness indicator to change visual states. A wetness indicator is considered a fullness indicator if it can indicate the degree to which a liquid bodily exudate has filled an absorbent article. A visual fullness indicator can indicate the presence of a liquid bodily exudate by a wet edge that moves along the indicator such that the indicator progressively changes visual states. A visual fullness indicator can include one or more visual fullness indicating areas. An indicating area is a defined continuous two-dimensional region, configured to indicate the presence of a liquid bodily exudate by its visual state. As examples, in various embodiments, an indicator can comprise a series of indicating areas or a pattern of indicating areas.

The figures of the present disclosure are intended to illustrate elements, their parts, and their relationships, as described in the specification; the figures are not intended to illustrate any particular relative or absolute size or dimension, unless otherwise stated in the text.

FIGS. 1A-2C illustrate various disposable wearable absorbent articles, each with one or more indicators. For clarity, FIGS. 1A-2C do not illustrate all details of the indicators or of the disposable wearable absorbent articles. Each indicator in FIGS. 1A-2C can be any embodiment of an indicator of the present disclosure.

FIG. 1A illustrates an outside perspective view of a front 101 and a side 103 of a pant-type disposable wearable absorbent article 100A formed for wearing. The pant-type disposable wearable absorbent article 100A includes a waist opening 107 and a leg opening 108. The absorbent article 100A includes a longitudinally oriented visual fullness indicator 131 disposed in the front 101.

Throughout the present disclosure, a reference to a pant-type disposable wearable absorbent article can refer to an embodiment that is side-fastenable or to an embodiment without fasteners. A reference to a pant-type disposable wearable absorbent article can also refer to an article with preformed waist and/or leg openings or to an embodiment that is not preformed. Thus, each embodiment of an absorbent article of the present disclosure that is described as pant-type can be configured in any of these ways, as will be understood by one of ordinary skill in the art.

Figure 1B:
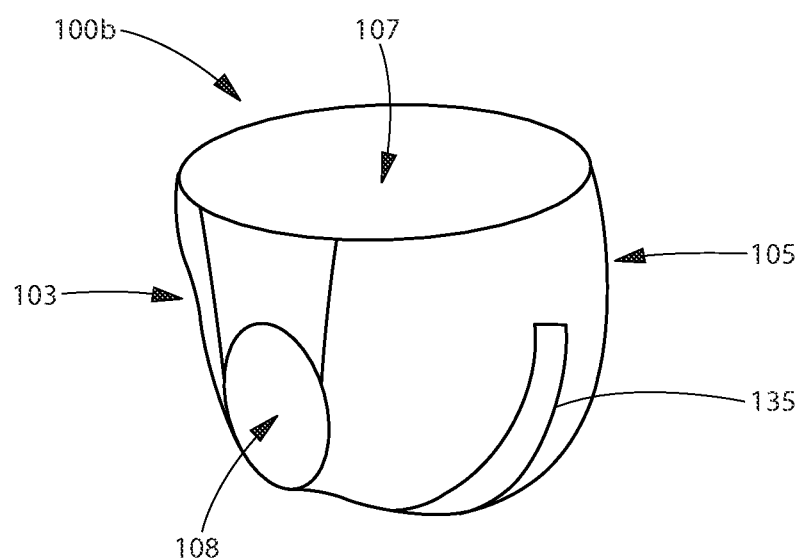
FIG. 1B illustrates a pant-type disposable wearable absorbent article with a visual fullness indicator in the back, according to embodiments of the present disclosure.

FIG. 1B illustrates an outside perspective view of a side 103 and a back 105 of a pant-type disposable wearable absorbent article 100B formed for wearing. The pant-type disposable wearable absorbent article 100B includes a waist opening 107 and a leg opening 108. The absorbent article 100B includes a longitudinally oriented visual fullness indicator 135 in the back 105.

Figure 1C:
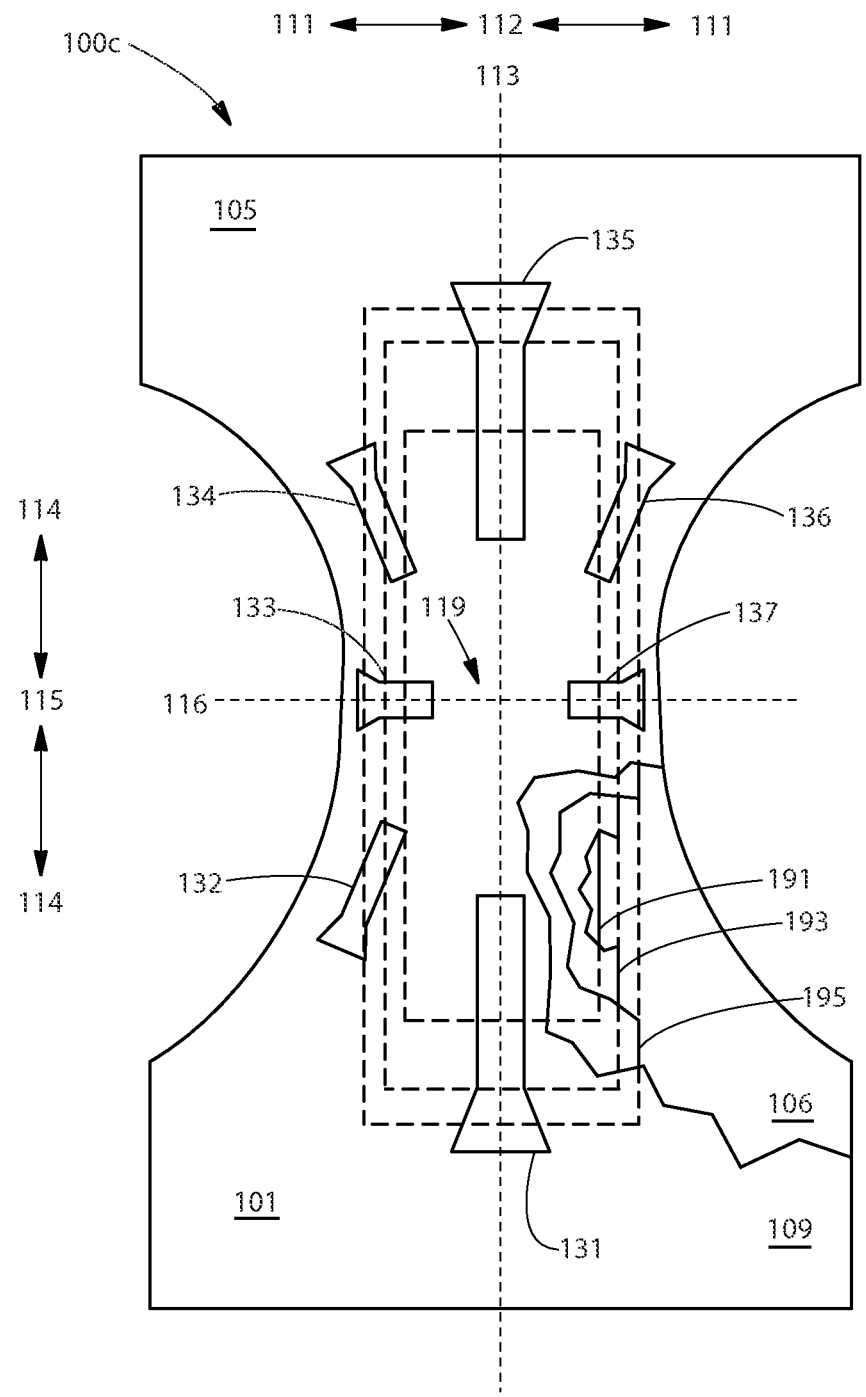
FIG. 1C illustrates a pant-type disposable wearable absorbent article with a number of visual fullness indicators, according to embodiments of the present disclosure.

FIG. 1C illustrates an outside plan view of a pant-type disposable wearable absorbent article 100C laid out flat. The disposable wearable absorbent article 100C includes a front 101 and a back 105, which are separated by a lateral centerline 116.

In FIG. 1C, a longitudinal centerline 113 and the lateral centerline 116 provide lines of reference for referring to relative locations of the disposable wearable absorbent article 100C. When a first location is nearer to the longitudinal centerline 113 than a second location, the first location can be considered laterally inboard 112 to the second location. Similarly, the second location can be considered laterally outboard 111 from the first location. When a third location is nearer to the lateral centerline 116 than a fourth location, the third location can be considered longitudinally inboard 115 to the fourth location. Also, the fourth location can be considered longitudinally outboard 114 from the third location.

A reference to an inboard location, without a lateral or longitudinal limitation, refers to a location of the disposable wearable absorbent article 100C that is laterally inboard and/or longitudinally inboard to another location. In the same way, a reference to an outboard location, without a lateral or longitudinal limitation, refers to a location of the disposable wearable absorbent article 100C that is laterally outboard and/or longitudinally outboard from another location.

Inboard and outboard can also be understood with reference to a center of a disposable wearable absorbent article. The longitudinal centerline 113 and the lateral centerline 116 cross at a center 119 of the disposable wearable absorbent article 100C. When one location is nearer to the center 119 than another location, the one location can be considered inboard to the other location. The one location can be inboard laterally, or longitudinally, or both laterally and longitudinally. The other location can be considered outboard from the one location. The other location can be outboard laterally, or longitudinally, or both laterally and longitudinally.

FIG. 1C includes arrows indicating relative directions for laterally outboard 111, laterally inboard 112, longitudinally outboard 114, and longitudinally inboard 115, each with respect to the disposable wearable absorbent article 100C. Throughout the present disclosure, a reference to a longitudinal dimension, measurement, line, or direction refers to a dimension, measurement, line, or direction that is substantially or completely parallel to the longitudinal centerline 113 and a reference to a lateral dimension, measurement, line, or direction refers to a dimension, measurement, line, or direction that is substantially or completely parallel to the lateral centerline 116. The terminology for describing relative locations, as discussed above, is used for disposable wearable absorbent articles throughout the present disclosure. This terminology can also be similarly applied to various other absorbent articles, as will be understood by one of ordinary skill in the art.

The disposable wearable absorbent article 100C includes a topsheet 106, an outer cover 109, an acquisition layer 191, a distribution layer 193, and an absorbent core 195. A portion of the outer cover 109 is shown as broken to illustrate a portion of the topsheet 106 and a portion of the absorbent core 195. A portion of the absorbent core 195 is shown as broken to illustrate a portion of the distribution layer 193. A portion of the distribution layer 193 is shown as broken to illustrate a portion of the acquisition layer 191.

The disposable wearable absorbent article 100C includes a number of visual fullness indicators in various exemplary locations and orientations. The disposable wearable absorbent article 100C includes a longitudinally oriented visual fullness indicator 131, along the longitudinal centerline 113 in the front 101. The front 101 also includes a first angled visual fullness indicator 132, oriented at an angle between the longitudinal centerline 113 and the lateral centerline 116.

The disposable wearable absorbent article 100C includes a first laterally oriented visual fullness indicator 133 and a second laterally oriented visual fullness indicator 137, each along the lateral centerline 116. The disposable wearable absorbent article 100C further includes a longitudinally oriented visual fullness indicator 135, along the longitudinal centerline 113 in the back 105. The back 105 also includes a third angled visual fullness indicator 134 and a fourth angled visual fullness indicator 136, each oriented at an angle between the longitudinal centerline 113 and the lateral centerline 116.

In the disposable wearable absorbent article 100C, the visual fullness indicators are oriented substantially radially out from the center 119. However, in addition to the locations and orientations illustrated in FIG. 1C, a visual fullness indicator of the present disclosure can be disposed in various alternate locations and orientations in an absorbent article, as will be understood by one of ordinary skill in the art. As an example, a visual fullness indicator can be disposed in a pant-type disposable wearable absorbent article at a location relative to a pee point for a wearer of the article.

Figure 2A:
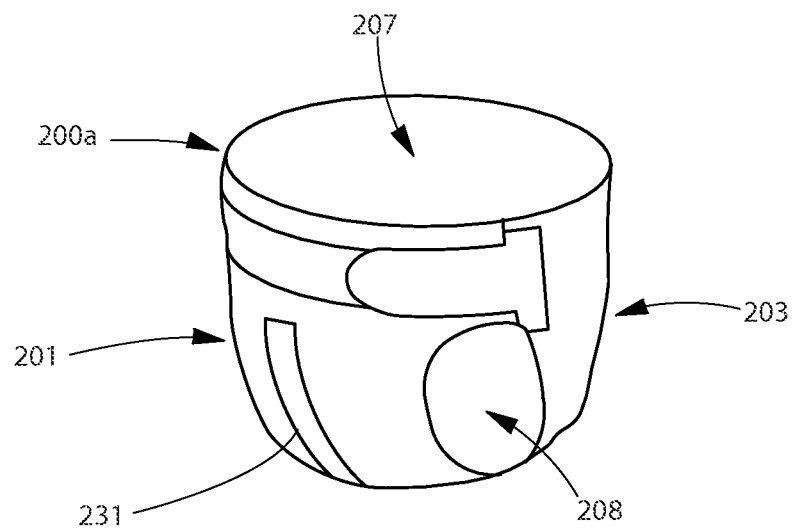
FIG. 2A illustrates a front-fastenable disposable wearable absorbent article with a visual fullness indicator in the front, according to embodiments of the present disclosure.

FIG. 2A illustrates an outside perspective view of a front 201 and a side 203 of a front-fastenable disposable wearable absorbent article 200A formed for wearing. The front-fastenable disposable wearable absorbent article 200A includes a waist opening 207 and a leg opening 208. The absorbent article 200A includes a longitudinally oriented visual fullness indicator 231 disposed in the front 201.

While the present disclosure refers to front-fastenable absorbent articles, the present disclosure also contemplates alternate embodiments of absorbent articles having multiple indicating widths, as described herein, wherein the absorbent articles are rear-fastenable. Thus, each embodiment of an absorbent article of the present disclosure that is described as front-fastenable can also be configured to be rear fastenable, as will be understood by one of ordinary skill in the art.

Figure 2B:
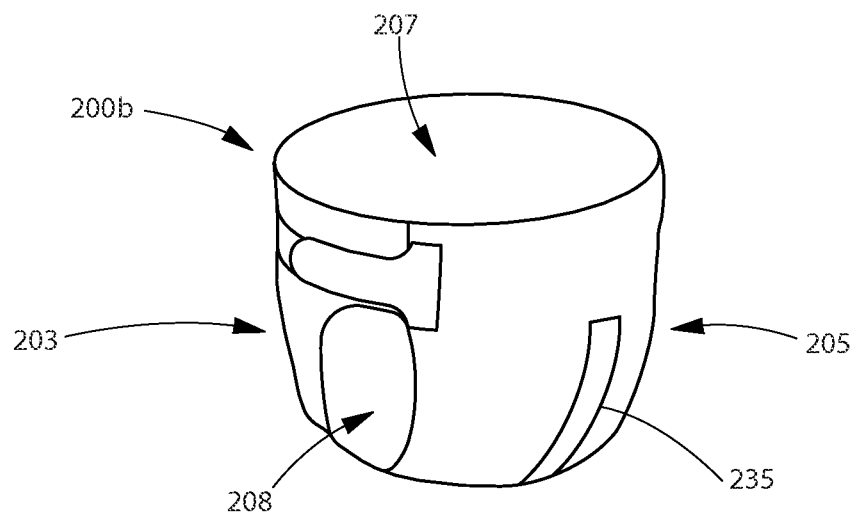
FIG. 2B illustrates a front-fastenable disposable wearable absorbent article with a visual fullness indicator in the back, according to embodiments of the present disclosure.

FIG. 2B illustrates an outside perspective view of a side 203 and a back 205 of a front-fastenable disposable wearable absorbent article 200B formed for wearing. The front-fastenable disposable wearable absorbent article 200B includes a waist opening 207 and a leg opening 208. The absorbent article 200B includes a longitudinally oriented visual fullness indicator 235 in the back 205.

Figure 2C:
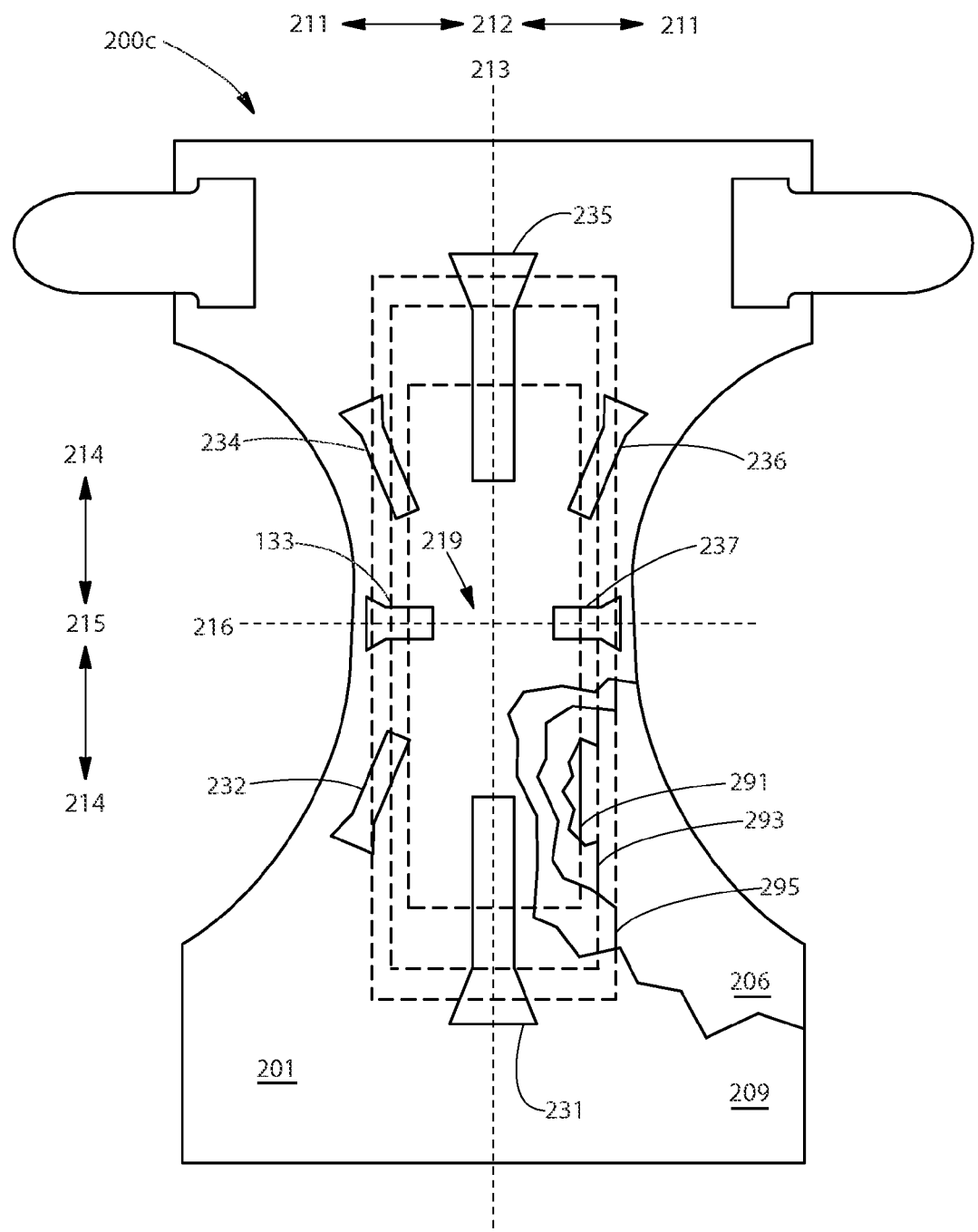
FIG. 2C illustrates a front-fastenable disposable wearable absorbent article with a number of visual fullness indicators, according to embodiments of the present disclosure.

FIG. 2C illustrates an outside plan view of a front-fastenable disposable wearable absorbent article 200C laid out flat. The disposable wearable absorbent article 200C includes a front 201, a back 205, a longitudinal centerline 213, and a lateral centerline 216.

The disposable wearable absorbent article 200C includes a topsheet 206, an outer cover 209, an acquisition layer 291, a distribution layer 293, and an absorbent core 295. A portion of the outer cover 209 is shown as broken to illustrate a portion of the topsheet 206 and a portion of the absorbent core 295. A portion of the absorbent core 295 is shown as broken to illustrate a portion of the distribution layer 293. A portion of the distribution layer 293 is shown as broken to illustrate a portion of the acquisition layer 291.

The disposable wearable absorbent article 200C includes a number of visual fullness indicators in various exemplary locations and orientations. The disposable wearable absorbent article 200C includes a longitudinally oriented visual fullness indicator 231, along the longitudinal centerline 213 in the front 201. The front 201 also includes a first angled visual fullness indicator 232, oriented at an angle between the longitudinal centerline 213 and the lateral centerline 216.

The disposable wearable absorbent article 200C includes a first laterally oriented visual fullness indicator 233 and a second laterally oriented visual fullness indicator 237, each along the lateral centerline 216. The disposable wearable absorbent article 200C further includes a longitudinally oriented visual fullness indicator 235, along the longitudinal centerline 213 in the back 205. The back 205 also includes a third angled visual fullness indicator 234 and a fourth angled visual fullness indicator 236, each oriented at an angle between the longitudinal centerline 213 and the lateral centerline 216.

In the disposable wearable absorbent article 200C, the visual fullness indicators are oriented substantially radially out from the center 219. However, in addition to the locations and orientations illustrated in FIG. 2C, a visual fullness indicator of the present disclosure can be disposed in various alternate locations and orientations in an absorbent article, as will be understood by one of ordinary skill in the art. As an example, a visual fullness indicator can be disposed in a front-fastenable disposable wearable absorbent article at a location relative to a pee point for a wearer of the article.

Figure 3A:
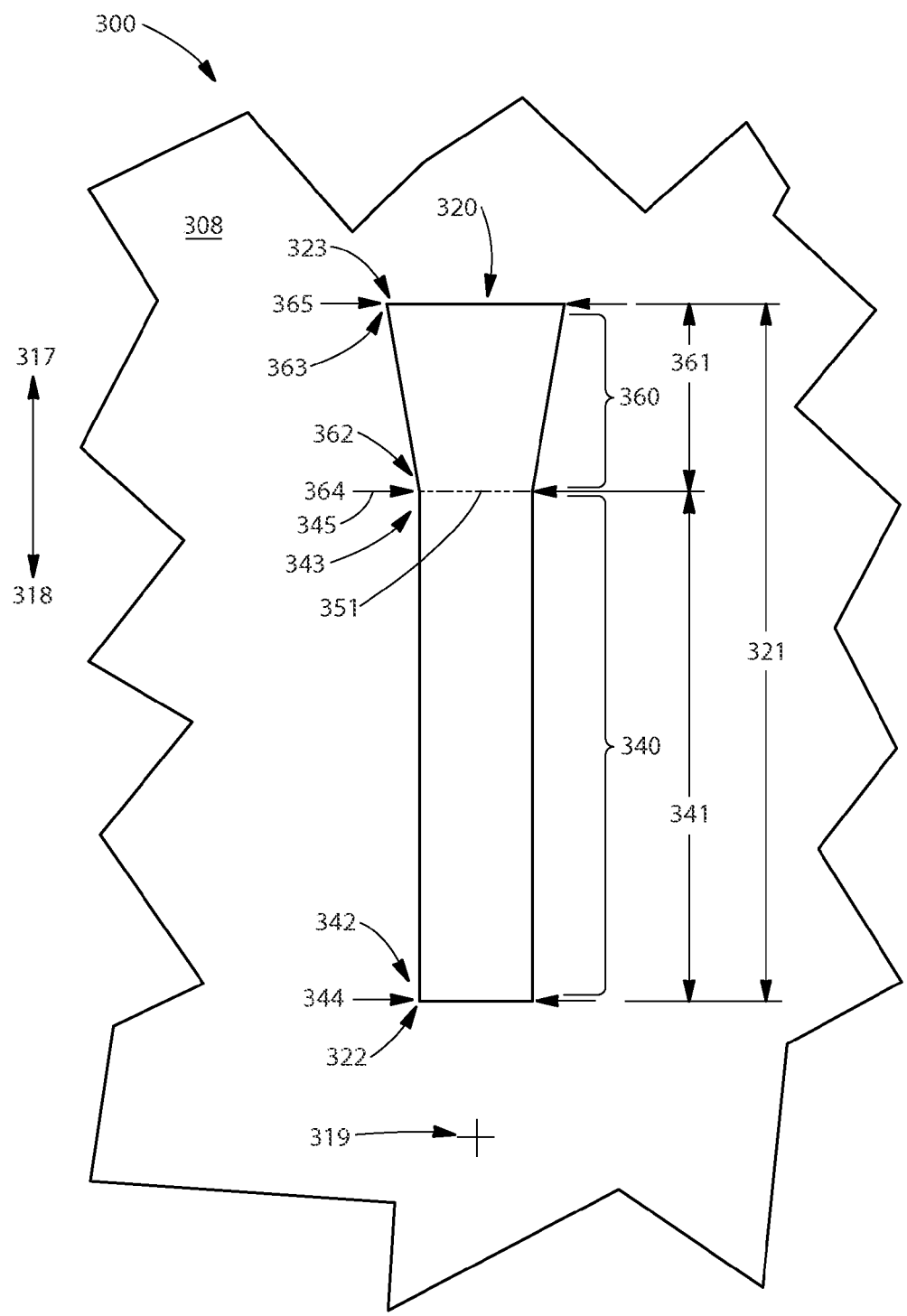
FIG. 3A illustrates a portion of an absorbent article with a visual fullness indicator having a first rectangular visual fullness indicating area with a narrower width and a second trapezoidal visual fullness indicating area with a wider outboard width, according to embodiments of the present disclosure.

FIG. 3A illustrates an outside plan view of a portion 308 of an absorbent article 300 laid out flat. In various embodiments, the absorbent article 300 can be a disposable wearable absorbent article, such as a pant-type disposable wearable absorbent article or a front-fastenable disposable wearable absorbent article. In FIG. 3A, outside edges of the portion 308 are broken lines, since the portion 308 is illustrated as separate from the rest of the absorbent article 300. For reference, FIG. 3A illustrates a center 319 of the absorbent article 300 and arrows indicating relative directions for outboard 317 and inboard 318 for the absorbent article 300.

The portion 308 of the absorbent article 300 includes a visual fullness indicator 320. The visual fullness indicator 320 is disposed offset from the center 319. In various embodiments, one or more parts of a visual fullness indicator can be disposed near, at, or overlapping a center of an absorbent article. For example, a single indicating area can extend from a front of an absorbent article, through the center of the absorbent article, to the back of the absorbent article. In such an embodiment, a farthest inboard point along the indicating area can be considered an inboard end of two indicators.

The visual fullness indicator 320 includes an inboard end 322 and an outboard end 323. The visual fullness indicator 320 has an overall indicator length 321, measured along the visual fullness indicator 320 from the inboard end 322 to the outboard end 323. The visual fullness indicator 320 has an overall shape that is substantially elongated.

In various embodiments a visual fullness indicator and/or an indicating area can have an overall shape that is more or less elongated. In some embodiments, part, or parts, or all of a visual fullness indicator and/or an indicating area can be straight, curved, angled, segmented, or any regular or irregular geometric shape (such as a square, rectangle, triangle, trapezoid, octagon, hexagon, star, half circle, a quarter circle, a half oval, a quarter oval, a radial pattern, etc.), a recognizable image (such as a letter, number, word, character, face of an animal, face of a person, etc.), or another recognizable image (such as a plant, a car, etc.), another shape, or combinations of any of these shapes. Also, in various embodiments, an indicator and/or an indicating area can have varying widths over part, or parts, or all of its length.

A visual fullness indicator is a visually distinct and recognizable pathway of one or more visual indicators and/or visual indicating areas. A pathway is recognizable in its visual context. In other words, a pathway is distinct and recognizable, when compared with the appearance of a surrounding area.

The pathway of a visual fullness indicator has two defined ends, a middle between the two ends, and a defined length from its one end to its other end. A visual fullness indicator can have one or more widths, each of which is less than its defined length.

A visual fullness indicator can be configured in various forms. For example, a visual fullness indicator can be formed by a single, continuous indicating area disposed along a pathway. As another example, a visual fullness indicator can be formed by a plurality of discrete indicators and/or discrete indicating areas disposed along a pathway.

The visual fullness indicator 320 includes, at least, a first visual fullness indicating area 340 and a second visual fullness indicating area 360. In various embodiments, a visual fullness indicator can include three or more visual fullness indicating areas.

The first visual fullness indicating area 340 includes a first area inboard end 342, a first area outboard end 343, and a first area overall length 341 measured along the first visual fullness indicating area 340 from the first area inboard end 342 to the first area outboard end 343. In a portion of the first visual fullness indicating area 340 at a location proximate to the first area inboard end 342, the first visual fullness indicating area 340 has an overall width 344. In a portion of the first visual fullness indicating area 340 at a location proximate to the first area outboard end 343, the first visual fullness indicating area 340 has an overall width 345. In the embodiment of FIG. 3A, the overall width 344 is equal to the overall width 345. Further, the first visual fullness indicating area 340 has a substantially uniform width along the entire first area overall length 341. The first visual fullness indicating area 340 has an overall shape that is substantially elongated and substantially rectangular. However, in some embodiments, a visual fullness indicating area can have various shapes and various widths over part, or parts, or all of its length, as described above in connection with the visual fullness indicator.

In addition to the first visual fullness indicating area 340, the visual fullness indicator 320 includes a second visual fullness indicating area 360. In the embodiment of FIG. 3A, the second visual fullness indicating area 360 is outboard 317 from the first visual fullness indicating area 340. The second visual fullness indicating area 360 includes a second area inboard end 362, a second area outboard end 363, and a second area overall length 361 measured along the second visual fullness indicating area 360 from the second area inboard end 362 to the second area outboard end 363. In the embodiment of FIG. 3A, the second area overall length 361 is less than the first area overall length 341. In some embodiments, a second area overall length can be equal to a first area overall length or greater than a first visual fullness indicating area overall length.

In a portion of the second visual fullness indicating area 360 at a location proximate to the second area inboard end 362, the second visual fullness indicating area 360 has an overall width 364. In the embodiment of FIG. 3A, the overall width 364 is equal to the overall width 345. In a portion of the second visual fullness indicating area 360 at a location proximate to the second area outboard end 363, the second visual fullness indicating area 360 has an overall width 365. In the embodiment of FIG. 3A, the overall width 365 is greater than each of the overall widths 344, 345, and 364. The second visual fullness indicating area 360 has an overall shape that is substantially elongated and substantially trapezoidal.

The visual fullness indicator 320 is in fluid communication with an absorbent core of the absorbent article 300 along the entire overall indicator length 321. In various embodiments, a visual indicator can be configured such that part, or parts, or substantially all, or all of the indicator is in fluid communication with an absorbent core. In some embodiments, a visual indicator can be configured such that part, or parts, or substantially all, or all of the indicator overlaps an absorbent core or such that part, or parts, or substantially all, or all of the indicator does not overlap an absorbent core.

Throughout the present disclosure, fluid communication refers to a configured structural relationship that allows a liquid substance to freely pass from one element or location to another element or location; however, one element or location is not necessarily considered to be in fluid communication with another element or location merely by being connected or joined to a common element through which liquid can possibly pass. This definition of fluid communication is further explained by the following examples.

For example, if one element is configured to be in direct physical contact with another element such that a liquid substance can freely pass from the one element through the contacting portions to the other element, then the elements can be considered to be in fluid communication. As another example, if one element is connected to another element by a means for fluid communication such that a liquid substance can freely pass from the one element through the means for fluid communication to the other element, then the elements can be considered to be in fluid communication.

As a further example, if one element is connected to a substrate and another element is connected to the same substrate, but the substrate does not allow a liquid substance to freely pass through, then the elements are considered to be out of fluid communication. This holds true even if liquid can possibly pass through the substrate, so long as the liquid cannot pass through freely. The above definition of fluid communication, as explained through these examples, will be understood by one of ordinary skill in the art.

Throughout the present disclosure, the term liquid bodily exudate refers to any bodily substances exuded in liquid form (e.g. urine) and/or any liquid-like bodily substances (e.g. runny feces).

In the embodiment of FIG. 3A, the first visual fullness indicating area 340 and the second visual fullness indicating area 360 are immediately adjacent to each other and in contact with each other at a shared boundary 351. The first visual fullness indicating area 340 is configured to be in direct physical contact with the second visual fullness indicating area 360 at the shared boundary 351.

In various embodiments, part, or parts, or all of a visual fullness indicating area can be configured to change from one or more initial visual states to one or more subsequent visual states. Also, in embodiments of the present disclosure, for a particular portion of a visual fullness indicating area, an initial visual state and a subsequent visual can each be any visual state, so long as the subsequent visual state is visually distinguishable from the first initial visual state.

Throughout the present disclosure, the term visual state refers to an appearance which can be perceived by an unaided human with normal vision in standard lighting conditions. A visual state can comprise one or more colors, variations of color(s), patterns, letters, numbers, symbol, designs, images, and/or other visual devices. Colors include well known colors such as red, orange, yellow, green, blue, purple, etc. Variations of a color include variations in chroma, hue, and brightness, among others. While these informal terms are used for ease of reference, embodiments of the present disclosure are intended to encompass all colors which can be perceived by an unaided human with normal vision in standard lighting conditions.

Throughout the present disclosure, visual states are considered visually distinguishable if they can be recognized as different on sight by an unaided human with normal vision in standard lighting conditions. As an example, an unaided human with normal vision in standard lighting conditions should be able to recognize blue and yellow as different colors on sight. Thus, the blue and the yellow would be considered visually distinguishable visual states. As another example, an unaided human with normal vision in standard lighting conditions may be able to recognize a light shade of orange and a dark shade of orange as different shades of a color on sight. Thus, the light shade of orange and the dark shade of orange would be considered visually distinguishable visual states. As a further example, an unaided human with normal vision in standard lighting conditions may be able to recognize a first pattern and a second pattern as different visual states on sight. Thus, the first pattern and the second pattern would be considered visually distinguishable visual states.

As a still further example, an unaided human with normal vision in standard lighting conditions should be able to recognize an area with letters and a blank area as different visual states on sight. Thus, the area with letters and the blank area would be considered visually distinguishable visual states. Similarly, an area with numbers, symbols, designs, images, and/or other visual devices would also be considered visually distinguishable from a blank area or from a uniformly colored area. In addition to these examples, there are many other possible visually distinguishable visual states, as will be understood by one or ordinary skill in the art.

There are several ways by which absorbent articles of the present disclosure can be configured to include indicating areas that change visual states when indicating the presence of a bodily exudate, as will be understood by one of ordinary skill in the art. For example, an absorbent article can be configured to include such visual fullness indicators as described in the following U.S. patents: U.S. Pat. No. 4,022,211, entitled "Wetness indicator for absorbent pads" issued on May 10, 1977 to Timmons, et al.; U.S. Pat. No. 4,231,370, entitled "Disposable diaper type garment having wetness indicator" issued on Nov. 4, 1980 to Mroz, et al.; U.S. Pat. No. 4,327,731, entitled "Moisture indicator" issued on May 4, 1982 to Powell; U.S. Pat. No. 4,681,576, entitled "Wetness indicating hot-melt adhesive" issued on Jul. 21, 1987 to Colon, et al.; U.S. Pat. No. 4,705,513, entitled "Disposable diaper with wetness indicator" issued on Nov. 10, 1987 to Sheldon, et al.; U.S. Pat. No. 4,738,674, entitled "Moisture indicator apparatus and method" issued on Apr. 19, 1988 to Todd, et al.; U.S. Pat. No. 4,743,238, entitled "Wetness indicating hot-melt adhesive" issued on May 10, 1988 to Colon et al.; U.S. Pat. No. 4,895,567, entitled "Wetness indicating hot-melt adhesive" issued on Jan. 23, 1990 to Colon et al.; U.S. Pat. No. 4,931,051, entitled "Wetness indicator" issued on Jun. 5, 1990 to Castello; U.S. Pat. No. 5,035,691, entitled "Hot melt moisture indicator material for disposable articles" issued on Jul. 30, 1991 to Zimmel, et al.; U.S. Pat. No. 5,066,711, entitled "Wetness indicating hot-melt adhesive" issued on Nov. 19, 1991 to Colon et al.; U.S. Pat. No. 5,089,548, entitled "Hot melt moisture indicator material for disposable articles" issued on Feb. 18, 1992 to Zimmel, et al.; U.S. Pat. No. 5,167,652, entitled "Moisture sensitive film" issued on Dec. 1, 1992 to Mueller; U.S. Pat. No. 5,342,861, entitled "Hot melt wetness indicator" issued on Aug. 30, 1994 to Raykovitz; U.S. Pat. No. 5,354,289 entitled "Absorbent product including super absorbent material and fluid absorption capacity monitor" issued on Oct. 11, 1994 to Mitchell, et al.; H1,376, entitled "Capacity indicia for absorbent articles" issued on Nov. 1, 1994 to Osborne, et al.; U.S. Pat. No. 5,647,863, entitled "Absorbent article with clean appearance and capacity signal means" issued on Jul. 15, 1997 to Hammons, et al.; U.S. Pat. No. 5,690,624, entitled "Disposable diaper" issued on Nov. 25, 1997 to Sasaki, et al.; U.S. Pat. No. 5,766,212, entitled "Disposable diaper" issued on Jun. 16, 1998 to Jitoe, et al.; U.S. Pat. No. 6,075,178, entitled "Absorbent article with wetness indicator" issued on Jun. 13, 2000; U.S. Pat. No. 6,515,194, entitled "Diaper having centrally-located chromatographic layer with peripherally-located wetness indicator" issued on Feb. 4, 2003 to Neading, et al.; U.S. Pat. No. 6,596,918, entitled "Absorbent articles having wetness indicating graphics and employing masking techniques" issued on Jul. 22, 2003 to Wehrle, et al.; U.S. Pat. No. 6,653,522, entitled "Hot melt adhesives based on sulfonated polyesters comprising wetness indicator" issued on Nov. 25, 2003 to Blumenthal, et al.; U.S. Pat. No. 6,772,708, entitled "Wetness indicator having improved colorant retention" issued on Aug. 10, 1994 to Klofta, et al.; U.S. Pat. No. 6,904,865, entitled "Wetness indicator having improved colorant retention and durability" issued on Jun. 14, 2005 to Klofta, et al.; U.S. Pat. No. 7,159,532, entitled "Wetness indicator having improved colorant retention and durability" issued on Jan. 9, 2007 to Klofta, et al.; U.S. Pat. No. 7,172,667, entitled "System and method for incorporating graphics into absorbent articles" issued on Feb. 6, 2007 to Vergona; U.S. Pat. No. 7,178,571, entitled "System and method for incorporating graphics into absorbent articles" issued on Feb. 20, 2007 to Vergona; U.S. Pat. No. 7,306,764, entitled "Wetness indicator" issued on Dec. 11, 2007 to Mody; and U.S. Pat. No. 7,332,642, entitled "Disposable absorbent articles having printed wetness indicators" issued on Feb. 19, 2008 to Liu, each of which is incorporated herein by reference.

In the embodiment of FIG. 3A, the first visual fullness indicating area 340 and the second visual fullness indicating area 360 are each configured to change from one or more initial visual states to one or more subsequent visual states when indicating the presence of a liquid bodily exudate.

An absorbent article can be configured such that part, or parts, or all of a visual indicating area is visible from outside of the absorbent article when the absorbent article is worn by a wearer. For example, a visual fullness indicating area can be visible when viewing an outside of an outer cover of an absorbent article. As a result, at least some of a subsequent visual state of the visual indicating area will be visible from outside of the absorbent article.

The absorbent article 300 can be configured such that part, or parts, or all of each of the first visual fullness indicating area 340 and the second visual fullness indicating area 360 is visible from outside of the absorbent article 300 when the absorbent article 300 is worn by a wearer. As a result, at least some of the first subsequent visual state and at least some of the second subsequent visual state will be visible from outside of the absorbent article 300.

The visual fullness indicator 320 can be configured such that the first visual fullness indicating area 340 and the second visual fullness indicating area 360 change visual states progressively and in sequence, as illustrated with FIGS. 3B-3E. First, the first visual fullness indicating area 340 can change from an initial visual state to a subsequent visual state when indicating the presence of a liquid bodily exudate to a first extent in an absorbent core of the absorbent article 300. Second, the second visual fullness indicating area 360 can change from an initial visual state to a subsequent visual state when indicating the presence of a liquid bodily exudate to a second extent in an absorbent core of the absorbent article 300. The partial or complete absence or presence of the subsequent visual state(s) on the visual fullness indicator 320 can indicate the fullness of the absorbent article 300.

Since the second visual fullness indicating area 360 has a wider width than the first visual fullness indicating area 340, the visual fullness indicator 320 is easy to understand. The narrower inboard widths and the wider outboard widths of the visual fullness indicator 320 can help provide certainty about the fullness of the absorbent article 300. By knowing the fullness of the absorbent article 300, the absorbent article 300 can be changed after a wearer has appropriately utilized its capacity and/or before it is likely to leak. The benefits of visual fullness indicating areas with wider outboard widths are similarly provided in the embodiments of FIGS. 4, 5, and 6, as described below.

FIGS. 3B-3E illustrate the visual fullness indicator 320 of the embodiment of FIG. 3A in various states of indication. The first visual fullness indicating area 340 and the second visual fullness indicating area 360 change visual states progressively and in sequence in the presence of a liquid bodily exudate to indicate the fullness of the absorbent article 300. In FIGS. 3B-3E, subsequent visual states are illustrated with hatch patterns.

FIG. 3B illustrates a subsequent state of indication for the visual fullness indicator 320 of FIG. 3A, wherein part of the first visual fullness indicating area 340 has changed from an initial visual state 328 to a subsequent visual state 329, to indicate the fullness of the absorbent article 300. In FIG. 3B, a liquid bodily exudate has passed through a portion of the absorbent core of the absorbent article 300 in sufficient concentration to cause a change in visual state from the inboard end 322 of the visual fullness indicator 320 up through part of the first visual fullness indicating area 340 to a wet edge 357B.

Throughout the present disclosure, a wet edge refers to a boundary along a visual wetness indicator of an absorbent article, wherein the boundary indicates an extent of the presence of a liquid bodily exudate. On the inboard side of the wet edge, the visual wetness indicator has experienced the presence of a liquid bodily exudate at a concentration that is sufficient to cause the visual wetness indicator to change visual states. On the outboard side of the wet edge, the visual wetness indicator has not yet experienced the presence of a liquid bodily exudate at a concentration that is sufficient to cause the visual wetness indicator to change visual states.

FIG. 3C illustrates a subsequent state of indication for the visual fullness indicator 320 of FIG. 3B, wherein all of the first visual fullness indicating area 340 has changed to the subsequent visual state 329 while all of the second visual fullness indicating area 360 remains in the initial visual state 328, to indicate the fullness of the absorbent article 300. In FIG. 3C, a liquid bodily exudate has passed through a portion of the absorbent core of the absorbent article 300 in sufficient concentration to cause a change in visual state from the inboard end 322 of the visual fullness indicator 320 up through all of first visual fullness indicating area 340 to a wet edge 357C.

FIG. 3D illustrates a subsequent state of indication for the visual fullness indicator 320 of FIG. 3C, wherein all of the first visual fullness indicating area 340 has changed to the subsequent visual state 329 and part of the second visual fullness indicating area 360 has changed from the initial visual state 328 to the subsequent visual state 329 to indicate the fullness of the absorbent article 300. In FIG. 3D, a liquid bodily exudate has passed through a portion of the absorbent core of the absorbent article 300 in sufficient concentration to cause a change in visual state from the inboard end 322 of the visual fullness indicator 320 up through all of the first visual fullness indicating area 340 and up through part of the second visual fullness indicating area 360 to a wet edge 357D.

FIG. 3E illustrates a subsequent state of indication for the visual fullness indicator 320 of FIG. 3D, wherein all of the first visual fullness indicating area 340 has changed to the subsequent visual state 329 and all of the second visual fullness indicating area 360 has changed to the subsequent visual state 329 to indicate the fullness of the absorbent article 300. In FIG. 3E, a liquid bodily exudate has passed through a portion of the absorbent core of the absorbent article 300 in sufficient concentration to cause a change in visual state from the inboard end 322 of the visual fullness indicator 320 up through all of the first visual fullness indicating area 340 and up through all of the second visual fullness indicating area 360 to a wet edge 357E, which is near the outboard end 323 of the visual fullness indicator 320.

Together, FIGS. 3B-3E illustrate that the visual fullness indicating areas of the visual fullness indicator 320 can change visual states progressively and in sequence in the presence of a liquid bodily exudate to indicate the degree to which a liquid bodily exudate has filled the absorbent article 300. In addition to indicating fullness, in embodiments of the present disclosure, such changes in visual state can also be understood as a signal that indicates the remaining absorbent capacity of an absorbent article and/or as a signal that indicates the risk that an absorbent article may leak.

An appropriate particular location and orientation, as well as specific dimensions and other physical characteristics, can be selected for visual fullness indicators of the present disclosure in order for an indicator to provide visual state change signals that indicate the degree of fullness, the remaining capacity, and/or the leakage risk for a particular absorbent article. In various embodiments, the absorbent article can include indicia correlating the visual state change signals with fullness, capacity, and/or leakage risk. The degree of fullness, the remaining capacity, and/or the leakage risk for a particular absorbent article can be determined as described in US non-provisional patent application entitled "Absorbent Articles with Primary and Secondary Indicating," filed on Dec. 23, 2009, which is incorporated herein by reference.

As a first example, in various embodiments, an inboard end of a visual fullness indicating area with a narrower width can be disposed at a particular location, such that, a change in visual state at that inboard end (i.e. a wet edge proximate to that inboard end) indicates that the absorbent article has: (a) a fullness of about 25%, 30%, 35%, 40%, 45%, 50%, 55%, 60%, 65%, 70%, 75%, 80%, 85%, or any integer of percentage between any of these values, or within any range using any of these values; (b) a remaining capacity of about 75%, 70%, 65%, 60%, 55%, 50%, 45%, 40%, 35%, 30%, 25%, 20%, 15%, or any integer of percentage between any of these values, or within any range using any of these values; and/or (c) a leakage risk of >0%, 5%, 10%, 15%, 20%, 25%, 30%, 35%, 40%, 45%, 50%, 55%, 60%, 65%, 70%, 75%, 80%, 85%, or any integer of percentage between any of these values, or within any range using any of these values. As used herein, the term "leakage risk" refers to the probability of a liquid bodily exudate leaking out of an absorbent article, while the article is being properly worn by a wearer of appropriate size, with such probability being measured in a sufficient number of articles being used by a sufficient number of wearers of appropriate size. For example, at least 100 users should use at least five days worth of articles to determine the probability of an article leaking.

An inboard end of a visual fullness indicating area with a narrower width can be disposed in an absorbent article at any of the following locations: 80 mm, 70 mm, 60 mm, 50 mm, 40 mm, 30 mm, 20 mm, 10 mm, or 5 mm inboard to an outer edge of an acquisition layer; at an outer edge of an acquisition layer; 80 mm, 70 mm, 60 mm, 50 mm, 40 mm, 35 mm, 30 mm, 25 mm, 20 mm, 15 mm, 10 mm, or 5 mm inboard to an outer edge of a distribution layer; at an outer edge of a distribution layer; 140 mm, 130 mm, 120 mm, 110 mm, 100 mm, 90 mm, 80 mm, 70 mm, 60 mm, 50 mm, 40 mm, 30 mm, 20 mm, 10 mm, or 5 mm inboard to an outer edge of an absorbent core; or at an outer edge of an absorbent core. An inboard end of a visual fullness indicating area with a narrower width can also be disposed in an absorbent article at any integer of mm between any of these values or within any range using any of these values.

As a second example, in various embodiments, an outboard end of a visual fullness indicating area with a narrower width can be disposed at a particular location, such that, a change in visual state at that outboard end (i.e. a wet edge proximate to that outboard end) indicates that the absorbent article has: (a) a fullness of 30%, 35%, 40%, 45%, 50%, 55%, 60%, 65%, 70%, 75%, 80%, 85%, 90%, or any integer of percentage between any of these values, or within any range using any of these values; (b) a remaining capacity of 70%, 65%, 60%, 55%, 50%, 45%, 40%, 35%, 30%, 25%, 20%, 15%, 10%, or any integer of percentage between any of these values, or within any range using any of these values; and/or (c) a leakage risk of 30%, 35%, 40%, 45%, 50%, 55%, 60%, 65%, 70%, 75%, 80%, 85%, 90%, or any integer of percentage between any of these values, or within any range using any of these values.

An outboard end of a visual fullness indicating area with a narrower width can be disposed in an absorbent article at any of the following locations: 70 mm, 60 mm, 50 mm, 40 mm, 30 mm, 20 mm, 10 mm, or 5 mm inboard to an outer edge of an acquisition layer; at an outer edge of an acquisition layer; 5 mm or 10 mm outboard from an outer edge of an acquisition layer; 70 mm, 60 mm, 50 mm, 40 mm, 30 mm, 25 mm, 20 mm, 15 mm, 10 mm, or 5 mm inboard to an outer edge of a distribution layer; at an outer edge of a distribution layer; 5 mm or 10 mm outboard from an outer edge of a distribution layer; 130 mm, 120 mm, 110 mm, 100 mm, 90 mm, 80 mm, 70 mm, 60 mm, 50 mm, 40 mm, 30 mm, 20 mm, 10 mm, or 5 mm inboard to an outer edge of an absorbent core; at an outer edge of an absorbent core; or 5 mm or 10 mm outboard from an outer edge of an absorbent core. An outboard end of a visual fullness indicating area with a narrower width can also be disposed in an absorbent article at any integer of mm between any of these values, or within any range using any of these values.

As a third example, in various embodiments, an inboard end of a visual fullness indicating area with a wider width can be disposed at a particular location, such that, a change in visual state at that inboard end (i.e. a wet edge proximate to that inboard end) indicates that the absorbent article has: (a) a fullness of 50%, 55%, 60%, 65%, 70%, 75%, 80%, 85%, 90%, 95% or any integer of percentage between any of these values, or within any range using any of these values; (b) a remaining capacity of 50%, 45%, 40%, 35%, 30%, 25%, 20%, 15%, 10%, 5%, or any integer of percentage between any of these values, or within any range using any of these values; and/or (c) a leakage risk of 10%, 20%, 30%, 40%, 50%, 60%, 70%, 80%, 90%, or any integer of percentage between any of these values, or within any range using any of these values A change in visual state at an inboard end of a visual fullness indicating area with a wider width may indicate a fullness that is less than, or equal to, or greater than a fullness indicated by a change in visual state at an outboard end of a visual fullness indicating area with a narrower width. A change in visual state at an inboard end of a visual fullness indicating area with a wider width may indicate a remaining capacity that is greater than, or equal to, or less than a remaining capacity indicated by a change in visual state at an outboard end of a visual fullness indicating area with a narrower width. A change in visual state at an inboard end of a visual fullness indicating area with a wider width may indicate a leakage risk that is greater than, or equal to, or less than a leakage risk indicated by a change in visual state at an outboard end of a visual fullness indicating area with a narrower width.

In various embodiments, a visual fullness indicating area with a wider width disposed in the back of an article can have an inboard end disposed with respect to a longitudinally outboard edge of an absorbent core disposed in the front of the article. In this way, the visual fullness indicating area with a wider width can be configured with respect to a point in the front/center of the article, where liquid bodily exudates are provided to the article by the wearer. As examples, a visual fullness indicating area with a wider width can be disposed in the back of an article with an inboard end of the indicating area disposed 275 mm, 270 mm, 260 mm, 250 mm, 240 mm, 230 mm, 220 mm, 210 mm, 200 mm, 190 mm, 180 mm, 170 mm, 160 mm, or 150 mm, from a longitudinally outboard edge of an absorbent core disposed in the front of the article. An inboard end of a visual fullness indicating area with a wider width can also be disposed in an absorbent article at any integer of mm between any of these values, or within any range using any of these values.

As a fourth example, in various embodiments, an outboard end of a visual fullness indicating area with a wider width can be disposed at a particular location, such that, a change in visual state at that outboard end (i.e. a wet edge proximate to that outboard end) indicates that the absorbent article has: (a) a fullness of 55%, 60%, 65%, 70%, 75%, 80%, 85%, 90%, 95%, about 100%, or any integer of percentage between any of these values, or within any range using any of these values; (b) a remaining capacity of 45%, 40%, 35%, 30%, 25%, 20%, 15%, 10%, 5%, about 0%, or any integer of percentage between any of these values, or within any range using any of these values; and/or (c) a leakage risk of 20%, 30%, 40%, 50%, 60%, 70%, 80%, 90%, about 100%, or any integer of percentage between any of these values, or within any range using any of these values. An outboard end of a visual fullness indicating area with a wider width can be disposed in an absorbent article at any of the following locations: 50 mm, 40 mm, 30 mm, 20 mm, 10 mm, or 5 mm inboard to an outer edge of an acquisition layer; at an outer edge of an acquisition layer; 5 mm, 10 mm, 20 mm, or 30 mm outboard from an outer edge of an acquisition layer; 50 mm, 40 mm, 30 mm, 25 mm, 20 mm, 15 mm, 10 mm, or 5 mm inboard to an outer edge of a distribution layer; at an outer edge of a distribution layer; 5 mm, 10 mm, 20 mm, or 30 mm outboard from an outer edge of a distribution layer; 110 mm, 100 mm, 90 mm, 80 mm, 70 mm, 60 mm, 50 mm, 40 mm, 30 mm, 20 mm, or 10 mm inboard to an outer edge of an absorbent core; at an outer edge of an absorbent core; or 5 mm, 10 mm, 20 mm, or 30 mm outboard from an outer edge of an absorbent core. An outboard end of a visual fullness indicating area with a wider width can also be disposed in an absorbent article at any integer of mm between any of these values, or within any range using any of these values.

It is contemplated that any of the exemplary embodiments described above can be applied in any workable combination to any relevant embodiment of the present disclosure.

Further, in some embodiments, instructions for the absorbent article can explain the correlation between the visual state change signals and fullness, capacity, and/or leakage risk. For example, such instructions can be provided on packaging for the absorbent article or on printed material accompanying the absorbent article. Still further, the correlation between the visual state change signals and fullness, capacity, and/or leakage risk can be communicated through various advertising media.

Further, while embodiments of the present disclosure are drawn toward absorbent articles having visual fullness indicating areas with relatively narrower inboard widths and relatively wider outboard widths, the present disclosure also contemplates alternate embodiments of absorbent articles having visual fullness indicating areas configured in an opposite manner, with relatively wider inboard widths and relatively narrower outboard widths. That is, for each disclosed visual fullness indicator and for each group of visual fullness indicating areas, the inboard and outboard directions can also be the reverse of the illustrated embodiment. Each embodiment of the present disclosure can be configured in this opposite manner, as will be understood by one of ordinary skill in the art. These alternate embodiments can also function to indicate different degrees of fullness, capacity, and/or leakage risk as described herein.

Figure 4:
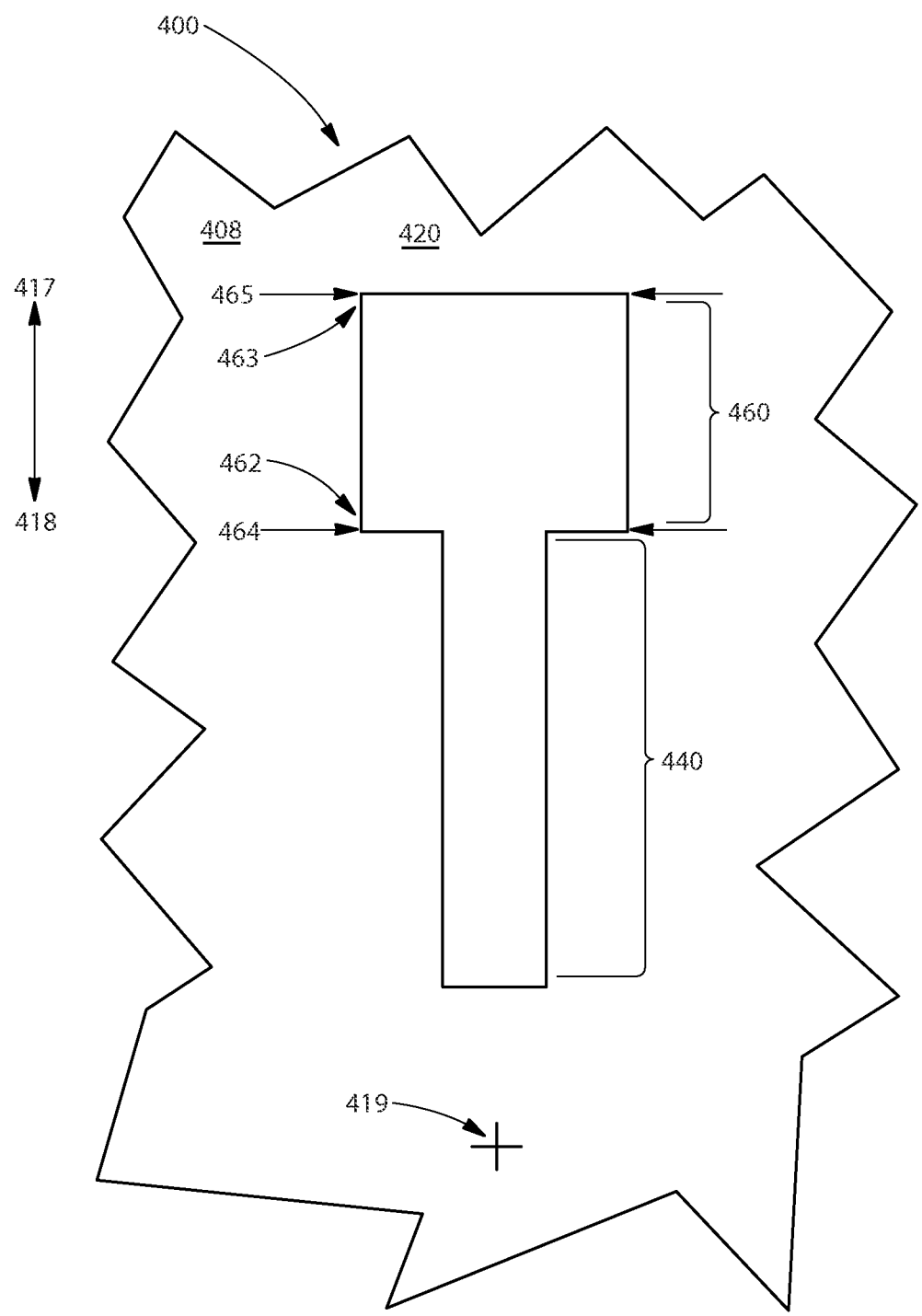
FIG. 4 illustrates a portion of an absorbent article with a visual fullness indicator having a first rectangular visual fullness indicating area with a narrower width and a second rectangular visual fullness indicating area with a wider width, according to embodiments of the present disclosure.

FIG. 4 illustrates an outside plan view of a portion 408 of an absorbent article 400 laid out flat. In various embodiments, the absorbent article 400 can be a disposable wearable absorbent article, such as a pant-type disposable wearable absorbent article or a front-fastenable disposable wearable absorbent article. For reference, FIG. 4 illustrates a center 419 of the absorbent article 400 and arrows indicating relative directions for outboard 417 and inboard 418 for the absorbent article 400. The portion 408 includes a first visual fullness indicating area 440 and a second visual fullness indicating area 460. Each of the elements of the embodiment of FIG. 4 is configured in the same way as the like-numbered element of the embodiment of FIG. 3A, except as noted below.

Throughout the present disclosure, the term "like-numbered" is intended to indicate a correspondence between labels of elements wherein the last two numbers in the labels of the elements are the same. Element labels are considered to be like-numbered despite differing numeral prefixes corresponding to figure numbers, and despite differing alphabetical suffixes corresponding to particular embodiments.

In a portion of the second visual fullness indicating area 460 at a location proximate to a second area inboard end 462, the second visual fullness indicating area 460 has an overall width 464. In a portion of the second visual fullness indicating area 460 at a location proximate to the second area outboard end 463, the second visual fullness indicating area 460 has an overall width 465. In the embodiment of FIG. 4, the overall width 464 is equal to the overall width 465. Further, the second visual fullness indicating area 440 has a substantially uniform width along the entire second area overall length. The second visual fullness indicating area 460 has an overall shape that is substantially elongated and substantially rectangular.

The first visual fullness indicating area 440 and the second visual fullness indicating area 460 can change visual states progressively and in sequence, similar to the embodiment illustrated with FIGS. 3B-3E. The partial or complete absence or presence of the subsequent visual state(s) in the first visual fullness indicating area 440 and/or the second visual fullness indicating area 460 can indicate the fullness of the absorbent article 400.

Since the second visual fullness indicating area 460 has a wider width than the first visual fullness indicating area 440, the visual fullness indicator 420 is easy to understand. The multiple indicating widths can help provide certainty about the fullness of the absorbent article 400. By knowing the fullness of the absorbent article 400, the absorbent article 400 can be changed after a wearer has appropriately utilized its capacity and/or before it is likely to leak.

Figure 5:
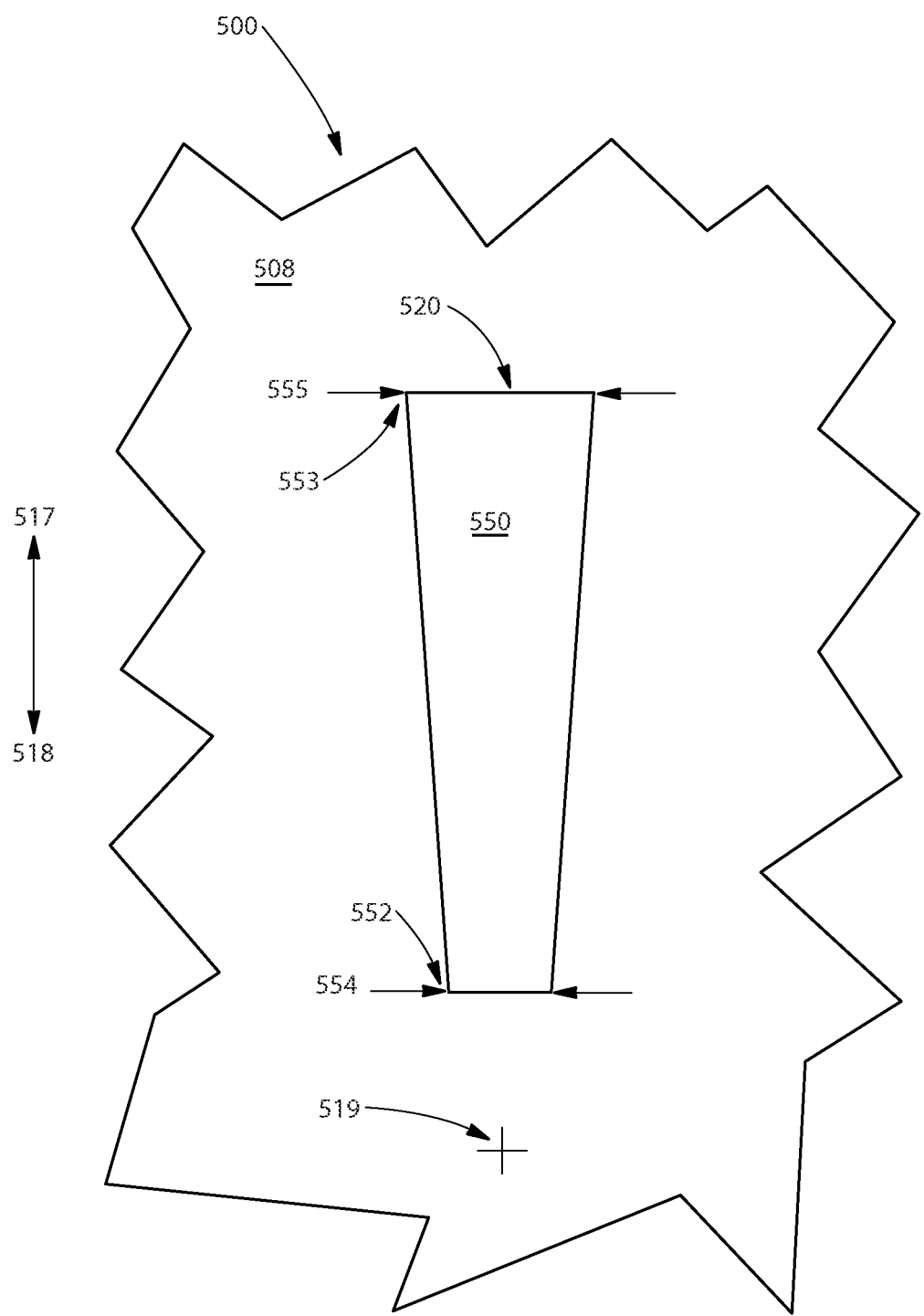
FIG. 5 illustrates a portion of an absorbent article with a visual fullness indicator having a trapezoidal visual fullness indicating area having an inboard end with a narrower width and an outboard end with a wider width, according to embodiments of the present disclosure.

FIG. 5 illustrates an outside plan view of a portion 508 of an absorbent article 500 laid out flat. In various embodiments, the absorbent article 300 can be a disposable wearable absorbent article, such as a pant-type disposable wearable absorbent article or a front-fastenable disposable wearable absorbent article. In FIG. 5, outside edges of the portion 508 are broken lines, since the portion 508 is illustrated as separate from the rest of the absorbent article 500. For reference, FIG. 5 illustrates a center 519 of the absorbent article 500 and arrows indicating relative directions for outboard 517 and inboard 518 for the absorbent article 500.

The portion 508 of the absorbent article 500 includes a visual fullness indicator 520. The visual fullness indicator 520 is disposed offset from the center 519. The visual fullness indicator 520 includes visual fullness indicating area 550.

The visual fullness indicating area 550 includes an area inboard end 552 and an area outboard end 553. In a portion of the visual fullness indicating area 550 at a location proximate to the area inboard end 552, the visual fullness indicating area 550 has an overall width 554. In a portion of the visual fullness indicating area 550 at a location proximate to the area outboard end 553, the visual fullness indicating area 550 has an overall width 555. In the embodiment of FIG. 5, the overall width 555 is greater than each of the overall widths 554. The visual fullness indicating area 550 has an overall shape that is substantially elongated and substantially trapezoidal. In an alternate embodiment, the area inboard end 552 can come to a point, such that the visual fullness indicating area 550 has an overall shape that is substantially triangular.

The visual fullness indicator 520 can indicate the presence of a liquid bodily exudate by a wet edge that continuously moves along the visual fullness indicator 520 such that the visual fullness indicator 520 changes colors progressively. The visual fullness indicating area 550 is configured to change from one or more initial visual states to one or more subsequent visual states when indicating the presence of a liquid bodily exudate.

The absorbent article 500 can be configured such that part, or parts, or all of each of the visual fullness indicating area 550 is visible from outside of the absorbent article 500 when the absorbent article 500 is worn by a wearer. As a result, at least some of the subsequent visual state(s) will be visible from outside of the absorbent article 500.

The visual fullness indicator 520 can be configured such that the visual fullness indicating area 550 changes visual states progressively, similar to the embodiment illustrated with FIGS. 3B-3E. First, the visual fullness indicating area 550 can change from an initial visual state to a subsequent visual state at the area inboard end 552 when indicating the presence of a liquid bodily exudate in the absorbent article 500. Second, the visual fullness indicating area 550 can change from an initial visual state to a subsequent visual state at the area outboard end 553 when indicating the presence of a liquid bodily exudate in the absorbent article 500. The partial or complete absence or presence of the subsequent visual state(s) on the visual fullness indicator 520 can indicate the fullness of the absorbent article 500.

Since the visual fullness indicator 520 has a wider outboard width and a narrower inboard width, the visual fullness indicator 520 is easy to understand. The multiple indicating widths can help provide certainty about the fullness of the absorbent article 500. By knowing the fullness of the absorbent article 500, the absorbent article 500 can be changed after a wearer has appropriately utilized its capacity and/or before it is likely to leak.

Figure 6:
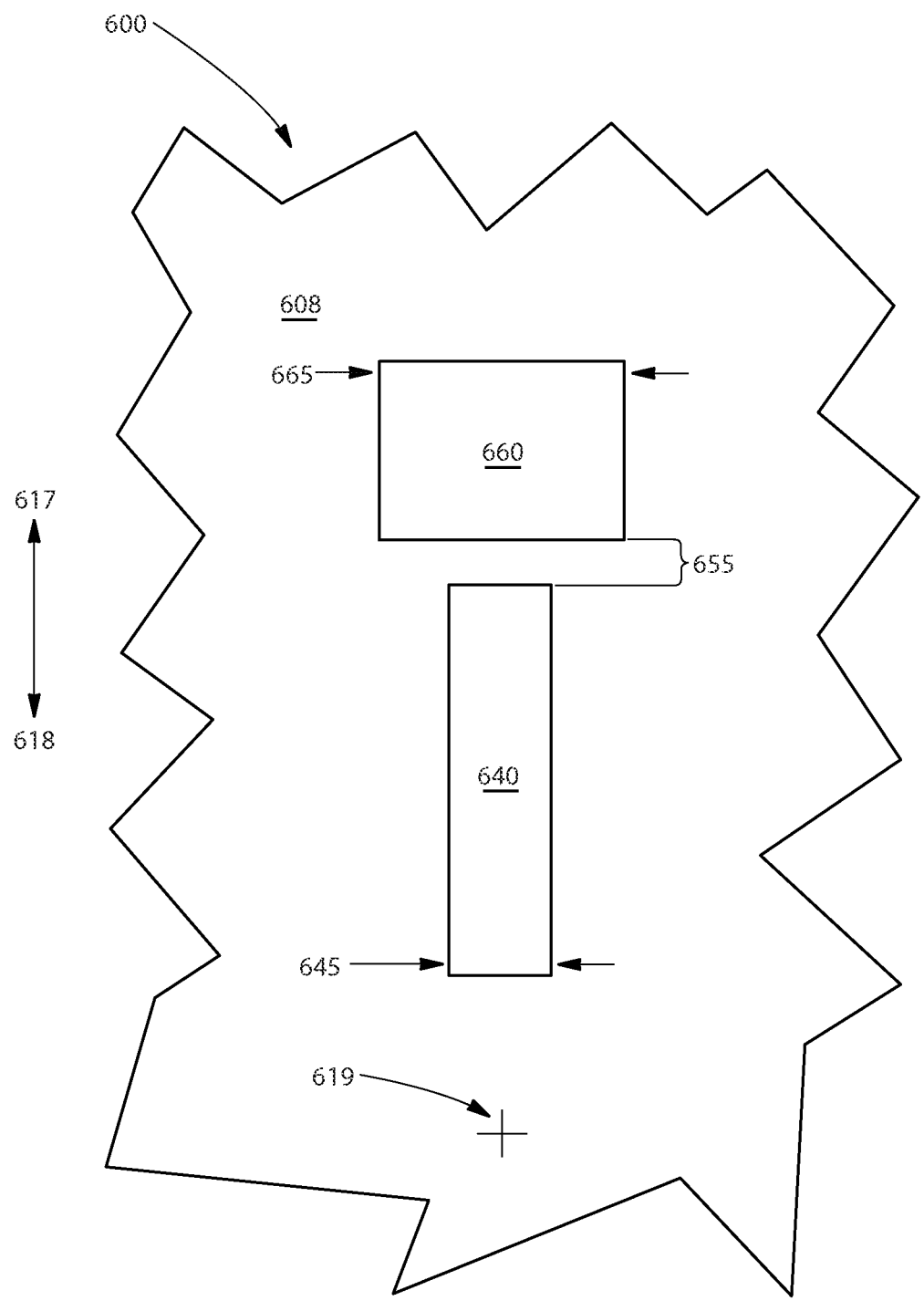
FIG. 6 illustrates a portion of an absorbent article having a first rectangular visual fullness indicating area with a narrower width and a second rectangular visual fullness indicating area with a wider width, wherein the first visual fullness indicating area is spaced apart from the second visual fullness indicating area, according to embodiments of the present disclosure.

FIG. 6 illustrates an outside plan view of a portion 608 of an absorbent article 600 laid out flat. In various embodiments, the absorbent article 600 can be a disposable wearable absorbent article, such as a pant-type disposable wearable absorbent article or a front-fastenable disposable wearable absorbent article. For reference, FIG. 6 illustrates a center 619 of the absorbent article 600 and arrows indicating relative directions for outboard 617 and inboard 618 for the absorbent article 600. The portion 608 includes a first visual fullness indicating area 640 and a second visual fullness indicating area 660. Each of the elements of the embodiment of FIG. 6 is configured in the same way as the like-numbered element of the embodiment of FIG. 4, except as noted below.

In the embodiment of FIG. 6, the second visual fullness indicating area 660 is spaced apart from the first visual fullness indicating area 640 by a separating portion 655. The first visual fullness indicating area 640 and the second visual fullness indicating area 660 can change visual states progressively and in sequence, similar to the embodiment illustrated with FIGS. 3B-3E. The partial or complete absence or presence of the subsequent visual state(s) in the first visual fullness indicating area 640 and/or the second visual fullness indicating area 660 can indicate the fullness of the absorbent article 600.

Since the second visual fullness indicating area 660 has a wider width than the first visual fullness indicating area 640, the visual fullness indicator 620 is easy to understand. The multiple indicating widths can help provide certainty about the fullness of the absorbent article 600. By knowing the fullness of the absorbent article 600, the absorbent article 600 can be changed after a wearer has appropriately utilized its capacity and/or before it is likely to leak.

Figure 7:
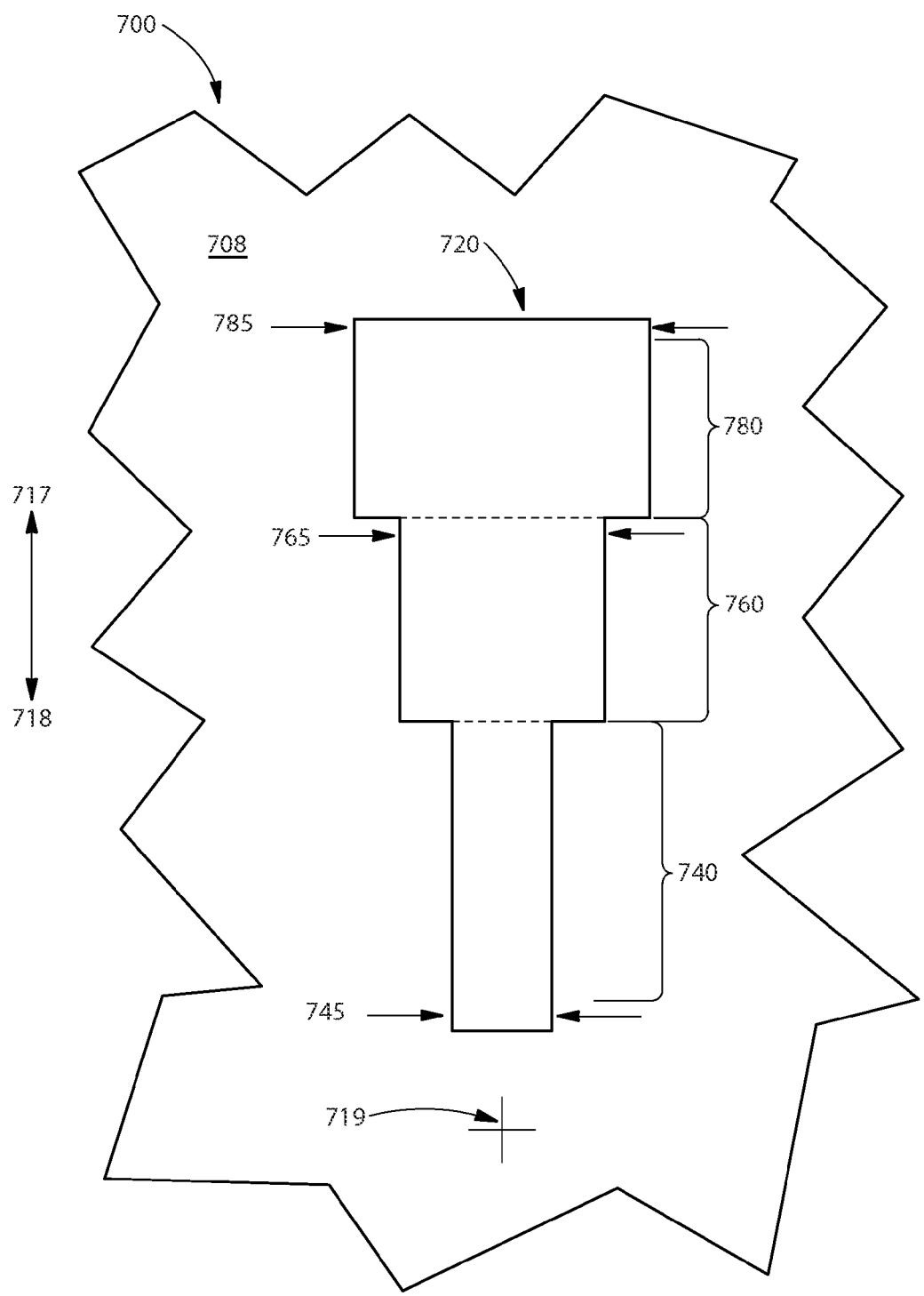
FIG. 7 illustrates a portion of an absorbent article having a first rectangular visual fullness indicating area with a narrower width, a second rectangular visual fullness indicating area with an intermediate width, and a third rectangular visual fullness indicating area with a wider width, according to embodiments of the present disclosure.

FIG. 7 illustrates an outside plan view of a portion 708 of an absorbent article 700 laid out flat. In various embodiments, the absorbent article 700 can be a disposable wearable absorbent article, such as a pant-type disposable wearable absorbent article or a front-fastenable disposable wearable absorbent article. For reference, FIG. 7 illustrates a center 719 of the absorbent article 700 and arrows indicating relative directions for outboard 717 and inboard 718 for the absorbent article 700. The portion 708 includes a visual fullness indicator 720, which includes, at least, a first visual fullness indicating area 740 and a second visual fullness indicating area 760. Each of the elements of the embodiment of FIG. 7 is configured in the same way as the like-numbered element of the embodiment of FIG. 4, except as noted below.

In addition to the first visual fullness indicating area 740 and the second visual fullness indicating area 760, the visual fullness indicator 720 includes a third visual fullness indicating area 780. In various embodiments, a visual fullness indicator can include four or more visual fullness indicating areas.

The third visual fullness indicating area 780 is outboard 717 from the second visual fullness indicating area 760. The third visual fullness indicating area 780 has an overall shape that is substantially elongated and substantially rectangular. The third visual fullness indicating area 780 has a substantially uniform width along its entire length.

In the embodiment of FIG. 5, the second visual fullness indicating area 760 and the third visual fullness indicating area 780 are immediately adjacent to each other, are in contact with each other at a shared boundary. In the embodiment of FIG. 7, the third visual fullness indicating area 780 is configured to change from one or more initial visual states to one or more subsequent visual states when indicating the presence of a liquid bodily exudate.

The absorbent article 700 can be configured such that part, or parts, or all of the third visual fullness indicating area 780 is visible from outside of the absorbent article 700 when the absorbent article 700 is worn by a wearer. As a result, at least some of the subsequent visual state(s) will be visible from outside of the absorbent article 700.

The first visual fullness indicating area 740, the second visual fullness indicating area 760, and the third visual fullness indicating area 780 can change colors progressively and in sequence, similar to the embodiment illustrated with FIGS. 3B-3E, but with the addition of a visual state change in the third visual fullness indicating area 580. The partial or complete absence or presence of the subsequent visual state(s) in the first visual fullness indicating area 740 and/or the second visual fullness indicating area 760 and/or the third visual fullness indicating area 780 can indicate the fullness of the absorbent article 700.

Since the third visual fullness indicating area 780 has a wider width than the second visual fullness indicating area 660 and the second visual fullness indicating area 760 has a wider width than the first visual fullness indicating area 740, the visual fullness indicator 720 is easy to understand. The multiple indicating widths can help provide certainty about the fullness of the absorbent article 700. By knowing the fullness of the absorbent article 700, the absorbent article 700 can be changed after a wearer has appropriately utilized its capacity and/or before it is likely to leak.

Figure 8:
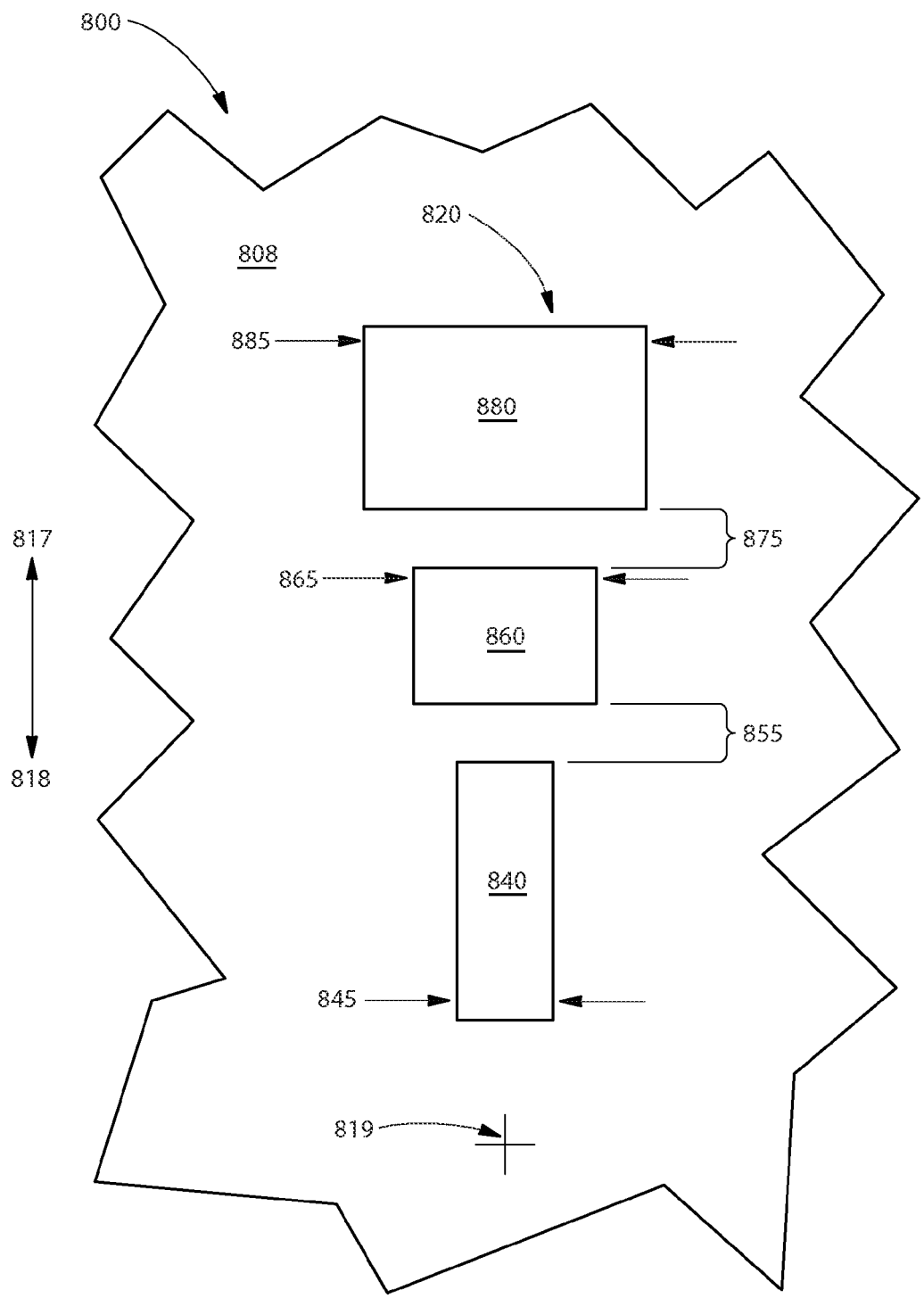
FIG. 8 illustrates a portion of an absorbent article having a first rectangular visual fullness indicating area with a narrower width, a second rectangular visual fullness indicating area with an intermediate width, and a third rectangular visual fullness indicating area with a wider width, wherein the first visual fullness indicating area, the second visual fullness indicating area, and the third visual fullness indicating area are spaced apart from each other, according to embodiments of the present disclosure.

FIG. 8 illustrates an outside plan view of a portion 808 of an absorbent article 800 laid out flat. In various embodiments, the absorbent article 800 can be a disposable wearable absorbent article, such as a pant-type disposable wearable absorbent article or a front-fastenable disposable wearable absorbent article. For reference, FIG. 8 illustrates a center 819 of the absorbent article 800 and arrows indicating relative directions for outboard 817 and inboard 818 for the absorbent article 800. The portion 808 includes a first visual fullness indicating area 840, a second visual fullness indicating area 860, and a third visual fullness indicating area 880. Each of the elements of the embodiment of FIG. 8 is configured in the same way as the like-numbered element of the embodiment of FIG. 7, except as noted below.

In the embodiment of FIG. 8, the second visual fullness indicating area 860 is spaced apart from the first visual fullness indicating area 840 by a separating portion 855, and the third visual fullness indicating area 880 is spaced apart from the second visual fullness indicating area 860 by a separating portion 875. In one alternate embodiment, a first visual fullness indicating area can be immediately adjacent to and in contact with a second visual fullness indicating area while a third visual fullness indicating area is still spaced apart from the second visual fullness indicating area. In another alternate embodiment, a second visual fullness indicating area can be immediately adjacent to and in contact with a third visual fullness indicating area while the second visual fullness indicating area is still spaced apart from a first visual fullness indicating area.

The first visual fullness indicating area 840, the second visual fullness indicating area 860, and the third visual fullness indicating area 880 can change visual states progressively and in sequence, as described in connection with the first visual fullness indicating area 740, the second visual fullness indicating area 760, and the third visual fullness indicating area 780 of the embodiment of FIG. 7.

The present disclosure includes absorbent articles with wetness indicators that are easy to understand. As a result, these wetness indicators can help provide certainty about the fullness of absorbent articles. By knowing how full an article is, the article can be changed after the wearer has appropriately utilized the capacity of the article. Also, by knowing how full an article is, the article can be changed before it is likely to leak.

Further, the present disclosure contemplates that an absorbent article, such as a disposable wearable absorbent article, can have one or more visual fullness indicators configured as described herein and further configured with various additional and/or alternate structures and/or functions as described below.

One or more embodiments of the present disclosure can be combined with one or more embodiments of U.S. non-provisional patent application Ser. No. 12/346,445 entitled "Disposable Wearable Absorbent Articles with Multiple Indicating Colors," filed on Dec. 30, 2008 and/or US non-provisional patent application entitled "Disposable Wearable Absorbent Articles with Multiple Indicating Colors," filed on Dec. 23, 2009, each of which is incorporated herein by reference. A disposable wearable absorbent article with multiple indicating widths can also have multiple indicating colors.

One or more embodiments of the present disclosure can be combined with one or more embodiments of U.S. non-provisional patent application Ser. No. 12/346,496 entitled "Disposable Wearable Absorbent Articles with Gender Specific Indicia," filed on Dec. 30, 2008 and/or U.S. non-provisional patent application entitled "Disposable Wearable Absorbent Articles with Gender Specific Indicia," filed on Dec. 23, 2009, each of which is incorporated herein by reference. A disposable wearable absorbent article with multiple indicating widths can also have gender specific indicia.

One or more embodiments of the present disclosure can be combined with one or more embodiments of U.S. non-provisional patent application Ser. No. 12/346,510 entitled "Disposable Wearable Absorbent Articles with Gender Specific Indicating," filed on Dec. 30, 2008 and/or US non-provisional patent application entitled "Disposable Wearable Absorbent Articles with Gender Specific Indicating," filed on Dec. 23, 2009, each of which is incorporated herein by reference. A disposable wearable absorbent article with multiple indicating widths can also have gender specific indicating.

One or more embodiments of the present disclosure can be combined with one or more embodiments of U.S. non-provisional patent application Ser. No. 12/346,520 entitled "Absorbent Articles with Patterns of Indicating," filed on Dec. 30, 2008 and/or US non-provisional patent application entitled "Absorbent Articles with Patterns of Indicating," filed on Dec. 23, 2009, each of which is incorporated herein by reference. A disposable wearable absorbent article with multiple indicating widths can also have patterns of indicating.

One or more embodiments of the present disclosure can be combined with one or more embodiments of U.S. provisional patent application Ser. No. 61/141,573 entitled "Absorbent Articles with Primary and Secondary Indicating," filed on Dec. 30, 2008 and/or US non-provisional patent application entitled "Absorbent Articles with Primary and Secondary Indicating," filed on Dec. 23, 2009, each of which is incorporated herein by reference. A disposable wearable absorbent article with multiple indicating widths can also have primary and secondary indicating.

One or more embodiments of the present disclosure can be combined with one or more embodiments of US non-provisional patent application entitled "Absorbent Articles with Primary and Secondary Indicia," filed on Dec. 23, 2009, which is incorporated herein by reference. A disposable wearable absorbent article with multiple indicating widths can also have primary and secondary indicia.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:
    an absorbent core with a total absorbent capacity;
    a longitudinally oriented first visual fullness indicator, the first visual fullness indicator having:
    a length;
    a first portion having a first overall width and a first location;
    a second portion having a second overall width and a second location, wherein the second location is outboard from the first location and the second overall width is wider than the first overall width;
    and an angled second visual fullness indicator.

2. The absorbent article of claim 1, which is a disposable absorbent article.

3. The disposable absorbent article of claim 2, which is a disposable wearable absorbent article.

4. The absorbent article of claim 3, wherein the first portion and the second portion are both part of a single visual fullness indicator.

5. The absorbent article of claim 4, wherein the single visual fullness indicator has an overall shape that is substantially elongated.

6. The absorbent article of claim 4, wherein the single visual fullness indicator has an overall shape that is substantially trapezoidal.

7. The absorbent article of claim 4, wherein the first location is proximate to an inboard end of the single visual fullness indicator.

8. The absorbent article of claim 4, wherein the second location is proximate to an outboard end of the single visual fullness indicator.

9. The absorbent article of claim 3, wherein the first portion is part of a first visual fullness indicating area, the second portion is part of a second visual fullness indicating area, and the first visual fullness indicating area is immediately adjacent to the second visual fullness indicating area.

10. The absorbent article of claim 3, wherein the first portion is included in a first visual fullness indicating area and the second portion is included in a second visual fullness indicating area, which is spaced apart from the first visual fullness indicating area.

11. The absorbent article of claim 10, wherein the first visual fullness indicating area has an overall shape that is substantially elongated.

12. The absorbent article of claim 3, wherein the first visual fullness indicator includes a third portion that has a third overall width and a third location, the third location being outboard from the second location and the third overall width being wider than the second overall width.

13. The absorbent article of claim 12, wherein the first portion is part of a first visual fullness indicating area, the second portion is part of a second visual fullness indicating area, the third portion is part of a third visual fullness indicating area, and the second visual fullness indicating area is immediately adjacent to the third visual fullness indicating area.

14. The absorbent article of claim 13, wherein the third visual fullness indicating area has an overall shape that is substantially elongated.

* * * * *